United States Patent [19]

Thompson et al.

[11] Patent Number: 5,468,483
[45] Date of Patent: Nov. 21, 1995

[54] BACILLUS THURINGIENSIS ANTI-GIARDIA TREATMENT

[75] Inventors: Mark Thompson, Del Mar; Frank H. Gaertner, San Diego, both of Calif.

[73] Assignee: Mycogen Corporation, San Diego, Calif.

[21] Appl. No.: 278,685

[22] Filed: Jul. 21, 1994

Related U.S. Application Data

[63] Continuation of Ser. No. 91,527, Jul. 12, 1993, abandoned, which is a continuation of Ser. No. 654,166, Feb. 12, 1991, abandoned, which is a continuation-in-part of Ser. No. 538,355, Jun. 14, 1990, abandoned.

[51] Int. Cl.$^6$ .................. A01N 63/02; A61K 39/07; A61K 38/16
[52] U.S. Cl. .................. 424/93.461; 514/2
[58] Field of Search .................. 424/93.461; 514/2

[56] References Cited

U.S. PATENT DOCUMENTS

| | | | |
|---|---|---|---|
| 4,695,455 | 9/1987 | Barnes et al. | 424/93.461 |
| 4,695,462 | 9/1987 | Barnes et al. | 424/93.461 |
| 4,861,595 | 8/1989 | Barnes et al. | 424/93.461 |
| 5,039,523 | 8/1991 | Payne et al. | 424/93.461 |

FOREIGN PATENT DOCUMENTS

| | | |
|---|---|---|
| 0358557 | 3/1990 | European Pat. Off. . |
| 0366397 | 5/1990 | European Pat. Off. . |

OTHER PUBLICATIONS

Casida, *App. Environ. Microbiol.* 55:1857–1859 (Aug. 1989).

Feitelson et al. *Bio/Tech.* 10:271–275 (Mar. 1992).

Aronson et al., *Microbiol. Rev.* 50:1–24 (Mar. 1986).

Prefontaine et al. *App. Environ. Microbiol.* 53:2808–2814 (Dec. 1987).

Visser, Bert, Ellie Munsterman, Andries Stoker and William G. Dirkse (1990) "A Novel Bacillus thuringiensis Gene Encoding a Spodoptera exiqua–Specific Crystal Protein", J. Bacteriology 72(12):6783–6788.

Bosse, M. L. Masson and R. Brousseau, (1990) "Nucleotide Sequence of a novel crystal protein gene isolated from *Bacillus thuringiensis* subspecies kenyae", Nuc. Acids. Res. 18(24):7443.

Gillin, F. D., M. J. Gault, A. F. Hofmann, D. Gurantz, J. F. Sauch (1986) "Biliary Lipids Support Serum–Free Growth of *Giardia lamblia*" Infection and Immunity 53(3):641–645.

Wolfe, M. S. (1978) "Current Concepts in Parasitology: Giardiasis," N. Engl. J. Med. 298(6):319–321.

Gaertner, F. H. (1990) "Cellular delivery systems for insecticidal proteins: living and non–living microorganisms," In *Controlled Delivery of Crop–Protection Agents*, R. M. Wilkins, ed., Taylor & Francis, Chapter 13.

Hofte, H., H. R. Whiteley (1989) "Insecticidal Crystal Proteins of *Bacillus thuringiensis*, " Microbiological Reviews 53(2):242–255.

*Primary Examiner*—Stephen G. Walsh
*Attorney, Agent, or Firm*—Saliwanchik & Saliwanchik

[57] ABSTRACT

The invention concerns a novel isolate of *Bacillus thuringiensis* which has activity against protozoans. Thus, this isolate, designated PS81F, or the purified protein toxin, or inclusion bodies from this isolate, can be used to treat humans and animals hosting a parasitic protozoan. Further, the gene encoding the toxin can be transferred to a suitable host via a biological vector, e.g., a plasmid or virus.

5 Claims, 6 Drawing Sheets

Fig. 1A

HD1 — WHITELEY'S "4.5" GENE
HD73 — ADANG'S "6.6" GENE
BTB — BULLA'S "5.3" GENE
81F — MYCOGEN'S 81F TOX GENE
BTE — HONEE'S ENTOMOCIDUS TOX GENE
HD2 — BRIZZARD'S HD2 TOX GENE

```
      1       5         10        15        20        25        30        35        40        45        50        55
HD1   M D N N P N I N E C I P Y N C L S N P E V E V L G G E R I E T G Y T P I D I S L S L T Q F L L S E F V P G A G
HD73  - - - - - - - - - - - - - - - - - - - - - - - - - - - - - - - - - - - - - - - - - - - - - - - - - - - - - - -
BTB   - - - - - - - - - - - - - - - - - - - - - - - - - - - - - - - - - - - - - - - - - - - - - - - - - - - - - - -
81F   - E I V N - Q - Q - V - - - - - N - - - N - I - D I - - S N S T = V A T N - A - E I S R = - - A S A T - I G -
BTE   - E E N N Q = - Q - - - - - - - - - - - E V L - D - - - - S - - N S S - - - - - - - V - - - V - N - - - - G -
HD2   - T S N R*- E - - I - N A V S N H S A Q M D L - P D A - - - D S*S T V Q T G I N I A G R I - G V L V - - F - -
               * K                                                  * L C I S E G N N I D P F V S A 56      60        65        70        75        80        85        90        95        100       105       110
HD1   F V L G L V D I I W G I F G P S Q W D A F P V Q I E Q L I N Q R I E E F A R N Q A I S R L E G L S N L Y Q I Y
HD73  - - - - - - - - - - - - - - - - - - - - - L - - - - - - - - - - - - - - - - - - - - - - - - - - - - - - - - -
BTB   - - - - - - - - - - - - - - - - - - - - - L - - - - - - - - - - - - - - - - - - - - - - - - - - - - - - - - -
81F   I L - - - F - A - - - S I - - - - - - - L - L E - - - L - - D - K - - - - - - - - - - - - - - - I - S - - G - -
BTE   - L V - - I - F V - - - V - - - - - - - - - L - - - - - - - - E - - G - - - - - A - - A N - - - - G - N F N - -
HD2  *Y S F = - - G E L - P R = - R D - - E I - L E H V - - - - - - Q - T - N - - - T - L A - - Q - - G D S F R A -
     * Q L A S F 111     115       120       125       130       135       140       145       150       155       160       165
HD1   A E S F R E W E A D P T N P A L R E E M R I Q F N D M N S A L T T A I P L L A V Q N Y Q V P L L S V Y V Q A A
HD73  - - - - - - - - - - - - - - - - - - - - - - - - - - - - - - - - - - - - - F - - - - - - - - - - - - - - - - -
BTB   - - - - - - - - - - - - - - - - - - - - - - - - - - - - - - - - - - - - - F - - - - - - - - - - - - - - - - -
81F   T - A - - - - - - - - - - - - - K - - - - T - - - - - - - I - V - - - - - F S - - - - - - - F - - - - A - - -
BTE   V - A - K - - - E - - N - - E T - T R V I D R - R I L D G L - E R D - - S F R I S G F E - - - - - - - A - - -
HD2   Q Q - L E D - L E N R D D A R T - S V L Y T - Y I A L E L D F L N - M - - F - I R - Q E - - - - M - - A - - -
```

```
     826                                                                880
HD1  G E P N R C A P H L E W N P D L D C S C R D G E K C A H H S H H F S L D I D V G C T D L N E D L G V W V I F K
HD73 - - - - - - - - - - - - - - - - - - - - - - - = - - - - - - - - - - - - - - - - - - - - - - - - - - - - - -
BTB  - - - - - - - - - - - - - - - - - - - - - - - = - - - - - - - - - - - - - - - - - - - - - - - - - - - - - -
81F  - - - - - - - - - - - - - - N - - - - - - - - = - - - - - - - - - - - T - - - - - - - - - - - H - - - - - - -
BTE  - - - A - - - - F - - - - - - - - - - - - - - = - - - - - - - - - - - - - - - - - - - - - - - - - - - - - - -
HD2  - - - - - - - - - - - - - - V - - - - - - - - = - - - - - - - - - - - - - - - - - - - - N - - - - - - - - V -

881                                                                935
HD1  I K T Q D G H A R L G N L E F L E E K P L V G E A L A R V K R A E K K W R D K R E K L E W E T N I V Y K E A K
HD73 - - - - - - - - - - - - - - - - - - - - - - - - - - - - - - - - - - - - - - - - - - - - - - - - - - - - - -
BTB  - - - - - - - - - Y - - - - - - - - - - - - - - - - - - - - - - - - - - - - - - - - - - - - - - - - - - - -
81F  - - - - - - - - - - - - - - - - - - - - - - - - - - - - - - - - - - - - - - - - - - Q L - - - - - - - K R - -
BTE  - - - - E - - - - - - - - - - - - I - - L - - - - - S - - - - - - - - - - - - - - C - Q L - - - - - - - - - -
HD2  - - - - - - - - - - - - - - - - - - - - L - - - - - - - - - - - - - - - - - - - - - - - - - - - - - - - - - -

936                                                                990
HD1  E S V D A L F V N S Q Y D Q L Q A D T N I A M I H A A D K R V H S I R E A Y L P E L S V I P G V N A A I F E E
HD73 - - - - - - - - - - - - - R - - - - - - - - - - - - - - - - - - - - - - - - - - - - - - - - - - - - - - - -
BTB  - A - - - - - - - - - - - R - - - - - - - - - - - - - - - - - - R - - - - - - - - - - - - - - - - - - - - - -
81F  - - - - - - - - - - - - - R V - - - - - - - - - - - - - - - - - - R - - - - - - - - S - - - - - - - - - - T -
BTE  - - - - - - - - - - - D - R - - - - - - - - - - - - - - - - L - - - - - - - - - - - - - - - - - - - - - - - -
HD2  - - - - - - - - - - - - - - - - - - - - - - - G - - - - - - - - - - - - - - - - - - - - - - P - - - - - - E -

991                                                                1045
HD1  L E G R I F T A F S L Y D A R N V I K N G D F N N G L S C W N V K G H V D V E E Q N N Q R S V L V L P E W E A
HD73 - - - - - - - - - - - - - - - - - - - - - - - - - - - - - - - - - - - - - - - - - - - - - - - - - - - - - -
BTB  - - - - - - - - - - - Y - - - - - - - - - - - - - - - - - - - - - - - - - - - - H - - - - - - - V - - - - - -
81F  - H - - - - - - - - I - - - - - - - - - - - - - - - - - L - - - - - - - - - - - - H - - - - I - V - - - - - -
BTE  - - - - - - - - - - - - - - - - - V - - - - - - - - - - T - - - - - - - - - S H - - - D - - I - - - - - - - -
HD2  - - - - - - - - - - - - - - - - - - - - - - - - - - - - - - - - - - - - - - - Q - - - - - - - - - - - - - - -
```

Fig. 1F

BACILLUS THURINGIENSIS ANTI-GIARDIA TREATMENT

CROSS REFERENCE TO A RELATED APPLICATION

This application is a continuation of application Ser. No. 08/091,527, filed Jul. 12, 1993, now abandoned, which is a continuation of application Ser. No. 07/654,166, filed Feb. 12, 1991, now abandoned, which is a continuation-in-part of application Ser. No. 07/538,355, filed Jun. 14, 1990, now abandoned.

BACKGROUND OF THE INVENTION

Diseases caused by pathogenic protozoa are important in both human and animal health. Species of Entamoeba, coccidia, Giardia, and Trichomonas are intestinal disease-causing parasites that are responsible for human morbidity and death, and for considerable economic loss in farm animals such as chickens and cattle (*Parasitic Protozoa*. 1977. Julius P. Kreier, Ed., Academic Press, NY; *In Vitro Cultivation of Protozoan Parasites*. 1983. James B. Jensen, Ed., CRC Press, FL). For illustration of the instant invention, we have chosen one such parasite, *Giardia lamblia*, which is responsible for giardiasis, an intestinal disease in humans (Gillin et al. [1986] Infect. Immun. 53:641–645).

*Giardia lamblia* is a flagellated protozoan that colonizes the upper small intestine of humans and causes the intestinal disease giardiasis. Giardia is a waterborne parasite that is especially prevalent in children, causing symptoms that include diarrhea, malabsorption, and failure to thrive. Symptoms may persist for years or may disappear spontaneously. The disease is both endemic and epidemic in the United States and is often acquired by campers who have drunk from wilderness streams or ponds (Wolfe, M. S. [1978] N. Engl. J. Med. 298:319–321). Travelers outside the United States, especially in underdeveloped countries, may acquire the disease by drinking local, untreated water.

In the upper small intestine, Giardia trophozoites are exposed to complex and highly variable mixtures of food and digestive agents, including enzymes and bile surfactants. It is in this environment, either attached to the mucosal epithelial cells or swimming in the intestinal fluid, that the parasite feeds and reproduces, and it is here that any protective or therapeutic agents must act. Current methods of treatment include the use of metronidazole or quinacrine, but both drugs have unpleasant side effects, and neither is 100% effective (Wolfe, supra).

*Bacillus thuringensis* (*B.t.*) with its growing list of sub-species, is known to produce a variety of crystalline protein inclusions that have insecticidal (Gaertner, F. H. [1990] *Controlled Delivery of Crop Protection Agents*, R. M. Wilkins, Ed., Taylor and Francis, PA, pp. 245–247) or nematicidal activities. The constituent biotoxins of the inclusions, known as δ-endotoxins, are highly specific in their activity, affecting only target insects or nematodes. The δ-endotoxins described to date (Hofte; H., H. R. Whitely [1989] *Microbiol. Rev.* 53:242–255) are non-toxic to higher animals, including humans.

BRIEF SUMMARY OF THE INVENTION

The present invention concerns a new isolate, designated *B.t.* PS81F, and mutants thereof, whose protein inclusion shows activity for the human intestinal pathogenic protozoan *Giardia lamblia*. Prior to the discovery of this isolate, it was not known or expected that the δ-endotoxins of *B.t.* would have activity for *G. lamblia* or other protozoa. The *B.t.* cells of the invention, the purified protein toxin, or the cell's proteinaceous inclusion bodies can be used as a prophylactic or therapeutic drug for the disease giardiasis. An oral dose taken prior to meals from about 1 to about 20 g of protein inclusion suspended in milk or other diluent can be used as either a protective or therapeutic dose for Giardia infection. Due to the non-toxic nature of the protein, the *B.t.* protein can be administered as frequently as needed to provide either protection or cure. Campers and travelers to underdeveloped countries can take prophylactic measures by taking daily oral doses during their stay and, in some instances, may want to continue administration for as long as one month after potential exposure. Diseased patients can take as much of the protein as needed and as often as needed to effect a cure, but a total oral dose per day would not normally exceed about 100 g.

Mutants of *B.t.* PS81F within the scope of the subject invention are those which have substantially the same anti-protozoan activity as *B.t.* PS81F. Mutants can be made by procedures well known in the art. For example, an asporogenous mutant can be obtained through ethylmethane sulfonate (EMS) mutagenesis of *B.t.* PS81F. Mutants also can be made using ultraviolet light and nitrosoquanidine by procedures well known in the art. The subject invention also concerns a gene encoding the toxin active against protozoan pests. This gene is obtained from the novel isolate *B.t.* PS81F. The gene can be transformed to suitable hosts via a plasmid vector.

BRIEF DESCRIPTION OF THE DRAWING

FIG. 1A, 1B, 1C, 1D, 1E, and 1F show a comparison of the deduced amino acid sequence of 81F with five other known *B.t.* endotoxins. Designations are as follows:

HD1 is the cryA1 toxin gene from *Bacillus thuringiensis* subsp. kurstaki HD1 (Brizzard and Whitley, Nucleic Acids Research 16(1988) 2723).

HD73 is the cryA3 gene from HD73.

BTB is the cryA2 gene from *B.t.* strain Berliner.

81F is a delta endotoxin gene from Mycogen's *B.t.* strain PS81F.

BTE is a delta endotoxin gene from *B.t.* subspecies entomocidus (Honee, Salm and Visser, Nucleic Acids Research 16(1988)6240).

HD2 is a delta endotoxin gene from *B.t.* strain HD2 (Brizzard and Whiteley, Nucleic Acids Research 16(1988)2723).

——— denote identical amino acid homologies.

=== denote gaps required to align sequences with HD1.

* * * * denote inserts required to align the sequences BTE and HD2 with HD1.

BRIEF DESCRIPTION OF THE SEQUENCES

SEQ ID NO. 1 discloses the DNA encoding the novel toxin.

SEQ ID NO. 2 discloses the amino acid sequence of the novel toxin.

SEQ ID NO. 3 is a composite of SEQ ID NO. 1 and SEQ ID NO. 2.

SEQ ID NO. 4 is a synthetic oligonucleotide constructed to one of the regions in the PS81F sequence.

DETAILED DISCLOSURE OF THE INVENTION

A subculture of *B.t.* PS81F was deposited in the permanent collection of the Northern Research Laboratory, U.S. Department of Agriculture, Peoria, Ill., USA on Oct. 7, 1988. The accession number is as follows:

*B.t.* PS81F—NRRL B-18424

The subject culture has been deposited under conditions that assure that access to the culture will be available during the pendency of this patent application to one determined by the Commissioner of Patents and Trademarks to be entitled thereto under 37 CFR 1.14 and 35 USC 122. The deposit is available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least 30 (thirty) years after the date of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it.

For general use, the *B.t.* antiprotozoan of the invention can be administered orally in a unit dosage form such as a capsule, bolus or tablet, or as a liquid drench when used as an antiprotozoan in mammals. The drench is normally a solution, suspension or dispersion of the active ingredient, usually in water, together with a suspending agent such as bentonite and a wetting agent or like excipient. Generally, the drenches also contain an antifoaming agent. Drench formulations generally contain from about 0.01 to 10% by weight of the active compound. Preferred drench formulations may contain from 0.1 to 1.0% by weight, the capsules and boluses comprise the active ingredient admixed with a carrier vehicle such as starch, talc, magnesium stearate, or dicalcium phosphate.

Where it is desired to administer the toxin compounds in a dry, solid unit dosage form, capsules, boluses or tablets containing the desired amount of active antiprotozoan usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the antiprotozoan agent, depending upon the factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or, optionally, fed separately. Alternatively, the antiprotozoan compounds may be administered to animals parenterally, for example, by intraluminal, intramuscular, intratracheal, or subcutaneous injection, in which event the active ingredient is dissolved or dispersed in a liquid carrier vehicle. For parenteral administration, the active material is suitably admixed with an acceptable vehicle, preferably of the vegetable oil variety, such as peanut off, cotton seed off and the like. Other parenteral vehicles, such as organic preparations using solketal, glycerol, formal and aqueous parenteral formulations, are also use& The antiprotozoan bioinclusions can be dissolved or suspended in the parenteral formulation for administration; such formulations generally contain from 0.01 to 10% by weight of the active compound.

When the antiprotozoan is administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like.

In addition to having antiprotozoan activity within the digestive tract of mammals, spores from the invention *B.t.*: isolate will pass through the animals' digestive tract, germinate and multiply in the feces, and thereby provide additional control of protozoans.

The gene(s) from the novel *B.t.* isolate of the subject invention can be introduced into microbes capable of occupying, surviving in, and proliferating in the phytosphere of plants according to the procedures disclosed in European Patent Application 0 200 344. Upon ingestion of such a plant by an animal hosting a protozoan, the protozoan-active toxin becomes available in the animal host to control the protozoan infestation.

The toxin gene obtained from the novel *B.t.* microbe of the subject invention can be introduced into a wide variety of microbial hosts. Such microbial hosts can be other *Bacillus thuringiensis* strains or other microbes, as disclosed herein. Further, the toxin gene can be engineered on a plasmid having a preferred promoter, or other desired regulatory element, and then the plasmid can be inserted into *B.t.* PS81F. Expression of the toxin gene results, directly or indirectly, in the intracellular production and maintenance of the antiprotozoan. With suitable hosts, e.g., Pseudomonas, the microbes can be applied to the situs of protozoans where they will proliferate and be ingested by the protozoans. The result is a control of the protozoans. Alternatively, the microbe hosting the toxin gene can be treated under conditions that prolong the activity of the toxin produced in the cell. The treated cell then can be applied to the environment of target pest(s). The resulting product retains the toxicity of the *B.t.* toxin.

Where the *B.t.* toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the antiprotozoan from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, particularly yeast, e.g., genera Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus,* and *Azotobacter vinlandii;* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans.* Of particular interest are the pigmented microorganisms.

A wide variety of ways are known and available for introducing the *B.t.* genes expressing the toxin into the microorganism host under conditions which allow for stable maintenance and expression of the gene. The transformants can be isolated in accordance with conventional ways, usually employing a selection technique, which allows for selection of the desired organism as against unmodified organisms or transferring organisms, when present. The transformants then can be tested for antiprotozoan activity.

Suitable host cells, where the antiprotozoan-containing cells will be treated to prolong the activity of the toxin in the cell when the then treated cell is applied to the environment of target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and -positive, include Enterobacteriaceae, such as Escherichia, Erwinia, Shigella, Salmonella, and Proteus; Bacillaceae; Rhizobiceae, such as Rhizobium; Spirillaceae, such as photobacterium, Zymomonas, Serratia, Aeromonas, Vibrio, Desulfovibrio, Spirillum; Lactobacillaceae; Pseudomonadaceae, such as Pseudomonas and Acetobacter; Azotobacteraceae and Nitrobacteraceae. Among eukaryotes are fungi, such as Phycomycetes and Ascomycetes, which includes yeast, such as Saccharomyces and Schizosaccharomyces; and Basidiomycetes yeast, such as Rhodotorula, Aureobasidium, Sporobolomyces, and the like.

Characteristics of particular interest in selecting a host cell for purposes of production include ease of introducing the *B.t.* gene into the host, availability of expression systems, efficiency of expression, stability of the antiprotozoan in the host, and the presence of auxiliary genetic capabilities. Characteristics of interest for use as an antiprotozoan microcapsule include protective qualities for the antiprotozoan, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as Rhodotorula sp., Aureobasidium sp., Saccharomyces sp., and Sporobolomyces sp.; phylloplane organisms such as Pseudomonas sp., Erwinia sp. and Flavobacterium sp.; or such other organisms as Escherichia, Lactobacillus sp., Bacillus sp., and the like. Specific organisms include *Pseudomonas aeruginosa, Pseudomonas fluorescens, Saccharomyces cerevisiae, Bacillus thuringiensis, Escherichia coli, Bacillus subtilis,* and the like.

The cell will usually be intact and be substantially in the proliferative form when treated, rather than in a spore form, although in some instances spores may be employed.

Treatment of the microbial cell, e.g., a microbe containing the *B.t.* toxin gene, can be by chemical or physical means, or by a combination of chemical and/or physical means, so long as the technique does not deleteriously affect the properties of the toxin, nor diminish the cellular capability in protecting the toxin. Examples of chemical reagents are halogenating agents, particularly halogens of atomic no. 17–80. More particularly, iodine can be used under mild conditions and for sufficient time to achieve the desired results. Other suitable techniques include treatment with aldehydes, such as formaldehyde and glutaraldehyde; anti-infectives, such as zephiran chloride and cetylpyridinium chloride; alcohols, such as isopropyl and ethanol; various histologic fixatives, such as Bouin's fixative and Helly's fixative (See: Humason, Gretchen L, Animal Tissue Techniques, W. H. Freeman and Company, 1967); or a combination of physical (heat) and chemical agents that preserve and prolong the activity of the toxin produced in the cell when the cell is administered to the host animal. Examples of physical means are short wavelength radiation such as gamma-radiation and X-radiation, freezing, UV irradiation, lyophilization, and the like.

The cells generally will have enhanced structural stability which will enhance resistance to environmental conditions. Where the antiprotozoan protein is in a proform, the method of inactivation should be selected so as not to inhibit processing of the proform to the mature form of the pesticide by the target pest pathogen. For example, formaldehyde will crosslink proteins and could inhibit processing of the proform of a polypeptide pesticide. The method of inactivation or killing retains at least a substantial portion of the bioavailability or bioactivity of the toxin.

Following are examples which illustrate procedures, including the best mode, for practicing the invention. These examples should not be construed as limiting. All percentages are by weight and all solvent mixture proportions are by volume unless otherwise noted.

EXAMPLE 1

Growth of Protozoal Cells

*Giardia lamblia* cells (received from Dr. Francis Gillin, Dept. of Pathology, University of California, San Diego, Calif.) were grown in 13 mm×100 mm borosilicate glass tubes in approximately 8 ml liquid medium. The medium was adjusted to a final pH of 7.1 to 7.2 with NaOH or HCl and contained in 100 ml: $K_2HPO_4$, 100 mg; $KH_2PO_4$, 60 mg; Biosate Peptone (BBL), 3.0 g; glucose, 1.0 g; NaCl, 200 mg; cysteine-HCl monohydrate, 200 mg; ascorbic acid, 20 mg; bovine bile, 50 mg; bovine serum (heat inactivated at 56° C. for 30 minutes), 10 ml. The medium was sterilized by filtration (0.2µ pore size). The antibiotics amikacin (Sigma) and piperacillin (Sigma) were added concentrations of 125 µg/ml and 500 µg/ml, respectively. In order to transfer the cells, they were detached from the walls of the borosilicate tube by chilling at least 7 minutes on ice, followed by inverting the tube 24 times. A small amount of medium and cells was transferred to about 8 ml of fresh medium, and the tube cap was screwed on tightly. The cells were grown at 37° C. and transferred to fresh medium when they reached confluency. Growth was monitored by microscopic examination.

EXAMPLE 2

Growth of *B.t.* PS81F (NRRL B-18424)

PS81F was grown at 30° C. on a rotary shaker at 200 rpm in 2 l baffled flasks containing 400 ml of broth for 64 hours. The broth medium contained Bacto peptone, 7.5 g/l; glucose, 1.0 g/l; $KH_2PO_4$, 3.4 g/l; $K_2HPO_4$, 4.35 g/l; "salt solution," 5.0 ml; and "$CaCl_2$ solution," 5.0 ml. The salt and $CaCl_2$ solutions were filter sterilized and added to the autoclaved broth at the time of inoculation. The "salt solution" contained in 100 ml: $MgSO_4\text{-}7H_2O$, 2.46 g; $MnSO_4\text{-}3H_2O$, 0.04 g; $ZnSO_4\text{-}7H_2O$, 0.28 g; and $FeSO_4\text{-}7H_2O$, 0.40 g. The "calcium solution" contained in 100 ml at pH 7.2: $CaCl_2\text{-}H_2O$, 3.66 g. *B.t.* spores and crystals obtained by the above fermentation were isolated by centrifugation at 7000 g for 20 minutes. Purification of the δ-endotoxin inclusions of various *B.t.* isolates was accomplished by banding the inclusions in NaBr density gradients according to the method of Pfannensteil, Ross, Kramer, and Nickerson ([1984] FEMS Microbiol. Lett. 21:39).

EXAMPLE 3

Assays

Protein concentrations were measured by the method of Lowry, Roseborough, Farr, and Randall (1951) J. Biol. Chem. 193:265.

The effect of *Bacillus thuringiensis* δ-endotoxin on *Giardia lamblia* viability was assayed as follows: Cells were grown at 37° C. in 1.7 ml of medium (defined above) in 2 ml screw-cap borosilicate glass vials (Wheaton) until they were subconfluent or confluent. Aqueous suspensions of purified protein crystal inclusions from *Bacillus thuringiensis* were added in a volume of up to 200 µl. Sterile distilled water was added at 200 µl or less to control cultures in place of the test suspension. Adherence of trophozoite cells to the walls of the culture vial was used as an indicator of cell viability and was monitored by phase contrast microscopy on an inverted microscope (Zeiss) for up to one week after toxin addition.

Verification that cell detachment activity was due to the action of δ-endotoxin protein was accomplished by destroying the activity with either proteolytic digestion or protein denaturation methods. Crystal protein preparations (1 mg/ml) were digested for 12 hours at 35° C. with rotary shaking at final protease concentrations of 5 or 50 units/ml in 55 mM Tris-HCl (pH 7.4). Controls included proteases with no crystal proteins, or crystal protein incubated at 35° C. without protease addition. Heat denaturation was accomplished by boiling samples in 55 mM Tris-HCl (pH 7.4) for 30 minutes. Treated protein was assayed, as described above, at a final concentration of about 100 µg/ml.

EXAMPLE 4

The subject invention can be used to control or eradicate a variety of protozoans. The following genera and species are examples of known parasite protozoans:

| | Genus | Specie |
|---|---|---|
| | Giardia | lamblia, duodenalis |
| | Toxoplasma | gondii |
| | Frankelia | buteonis |
| | Hammondia | hammondi, heydorni, pardalis |
| Coccidia | Isospora | belli, felis, rivolta, canis, ohioensis |
| | Besnoita | darlingi, jellisoni, besnoiti |
| | Eimeria | tenella (numerous other species) |
| | Entamoeba | histolytica, hartmanni, coli, gingivalis, invadens |
| | Trichomonas | fecalis, vaginalis, gallinae, foetis, suis, tenax |
| | Pentatrichomonas | hominis |

Results

Inclusions from isolate *B.t.* PS81F repeatedly killed Giardia at concentrations from about 100 µg/ml to about 1140 µg/ml. Lower concentrations appeared to be ineffective.

The cell detachment activity observed with the inclusions of isolate *B.t.* PS81F was shown to be due to a protein toxin by inactivating the toxin with either proteolytic digestion or by heat inactivation. Toxicity, as judged by the lack of cell adherence, was abolished by digestion with chymotrypsin or papain at 5 units/ml or by boiling the samples. Thermolysin at 50 units/ml had no visible effect. In addition, common *B.t.* strains such as *B.t.* subsp. *kurstaki* strain HD1 and subsp. *israelensis* strain HD567 were inactive at similar body inclusion concentrations.

EXAMPLE 5

Cloning of Novel Toxin Gene and Transformation into *Escherichia coli*

Total cellular DNA was prepared by growing the cells of *B. thuringiensis* HD-1 and the novel *B.t.* PS81F to a low optical density ($OD_{600}=1.0$) and recovering the cells by centrifugation. The cells were protoplasted in TES buffer (30 mM Tris-Cl, 10 mM EDTA, 50 mM NaCl, pH=8.0) containing 20% sucrose and 50 mg/ml lysozyme. The protoplasts were lysed by addition of SDS to a final concentration of 4%. The cellular material was precipitated overnight at 4° C. in 100 mM final concentration neutral potassium chloride. The supernate was extracted twice with phenol/chloroform (1:1). The DNA was precipitated in ethanol and purified by isopycnic banding on a cesium chloride gradient.

Total cellular DNA from each (PS81F and HD-1) was digested with EcoRI and separated by electrophoresis on a 0.8% Agarose-TAE-buffered gel. A Southern blot of the gel was probed with the NsiI to NsiI fragment of the toxin gene contained in plasmid pM3,130-7 of NRRL B-18332 and the NsiI to KpnI fragment of the "4.5 Kb class" toxin gene (Kronstad and Whitely [1986] Gene USA 43:29–40). These two fragments were combined and used as the probe. Results show that hybridizing fragments of PS81F are distinct from those of HD-1. Specifically, a 3.5 Kb hybridizing band in PS81F was detected instead of the 300 bp larger 3.8 Kb hybridizing band seen in HD-1.

Two hundred micrograms of PS81F total cellular DNA was digested with EcoRI and separated by electrophoresis on a preparative 0.8% Agarose-TAE gel. The 3.0 Kb to 4.0 Kb region of the gel was cut out and the DNA from it was electroeluted and concentrated using an ELUTIP™-d (Schleicher and Schuell, Keene, NH) ion exchange column. The isolated EcoRI fragments were ligated to LAMBDA ZAP™ EcoRI arms (Stratagene Cloning Systems, La Jolla, Calif.) and packaged using GIGAPACK GOLD™ extracts. The packaged recombinant phage were plated with *E. coli* strain BB4 (Stratagene) to give high plaque density. The plaques were screened by standard nucleic acid hybridization procedure with radiolabeled probe. The plaques that hybridized were purified and re-screened at a lower plaque density. The resulting purified phage were grown with R408 M13 helper phage (Stratagene) and the recombinant BLUE-SCRIPT™ (Stratagene) plasmid was automatically excised and packaged. The "phagemid" was re-infected in XL1-Blue *E. coli* cells (Stratagene) as part of the automatic excision process. The infected XL1-Blue cells were screened for ampicillin resistance and the resulting colonies were analyzed by standard miniprep procedure to find the desired plasmid. The plasmid, designated pM5,31-1, contained an approximate 3.5 Kb EcoRI insert and was sequenced using Stratagene's T7 and T3 primers plus a set of existing *B.t.* endotoxin oligonucleotide primers. About 1.7 Kb of the toxin gene was sequenced and data analysis comparing PS81F to other cloned *B.t.* endotoxin genes showed that the PS81F sequence was unique. A synthetic oligonucleotide (SEQ ID NO. 4 GCTGAAGAACTTCCTATTCGTGGTG-GTGAGC) was constructed to one of the regions in the PS81F sequence that was least homologous relative to other existing *B.t.* endotoxin genes.

Figure 1B:
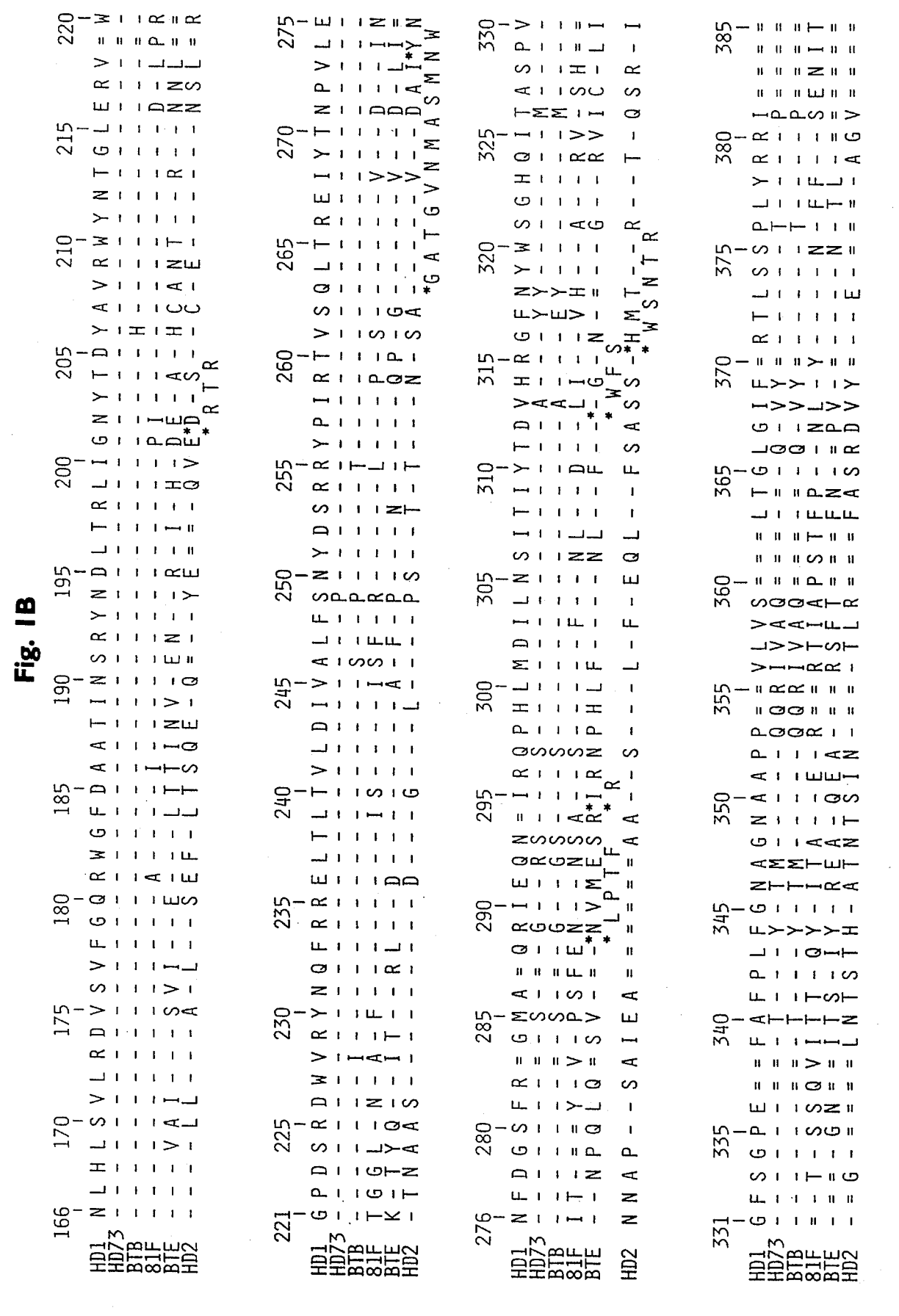
Figure 1C:
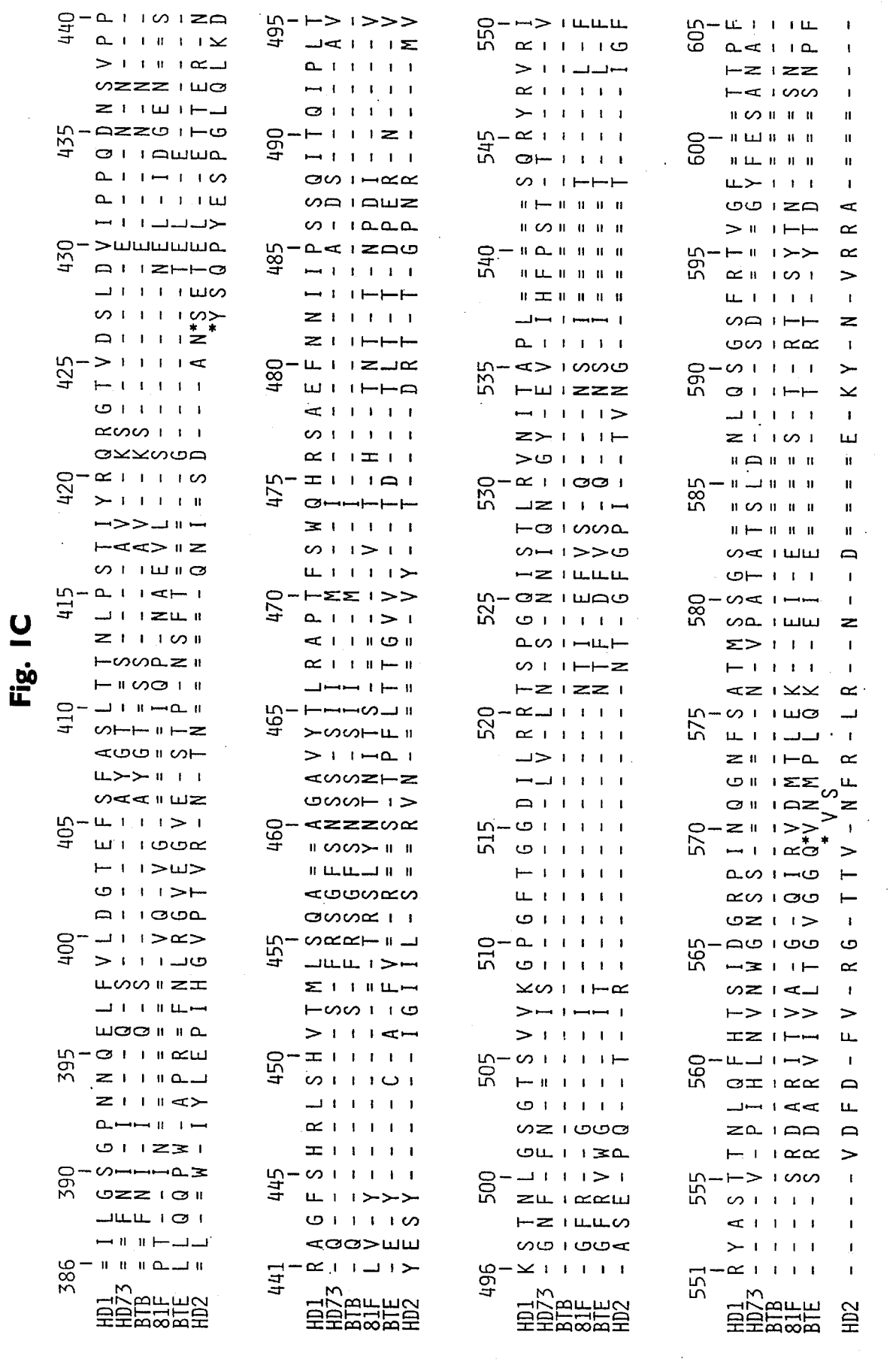
Figure 1D:
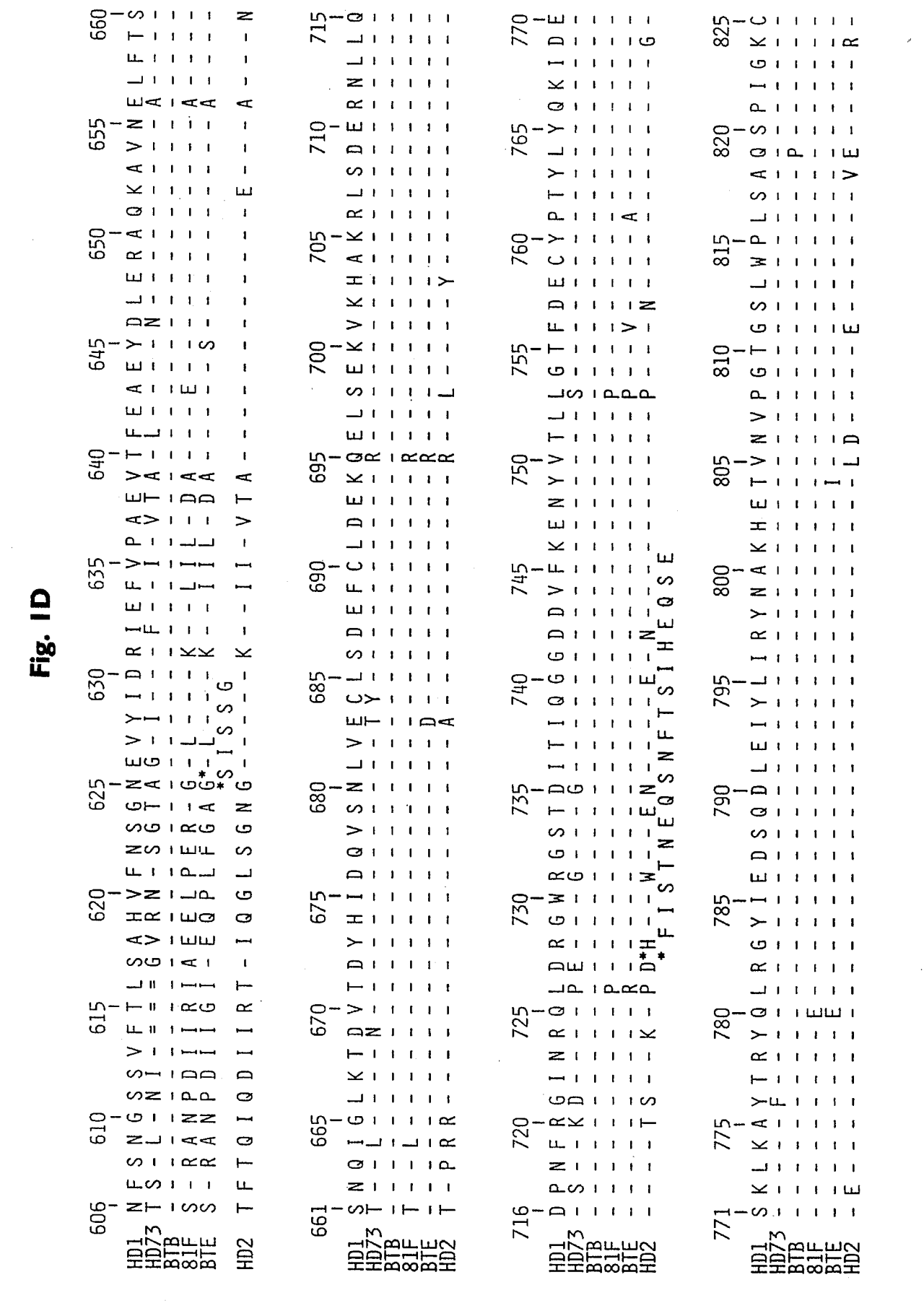
Figure 1F:
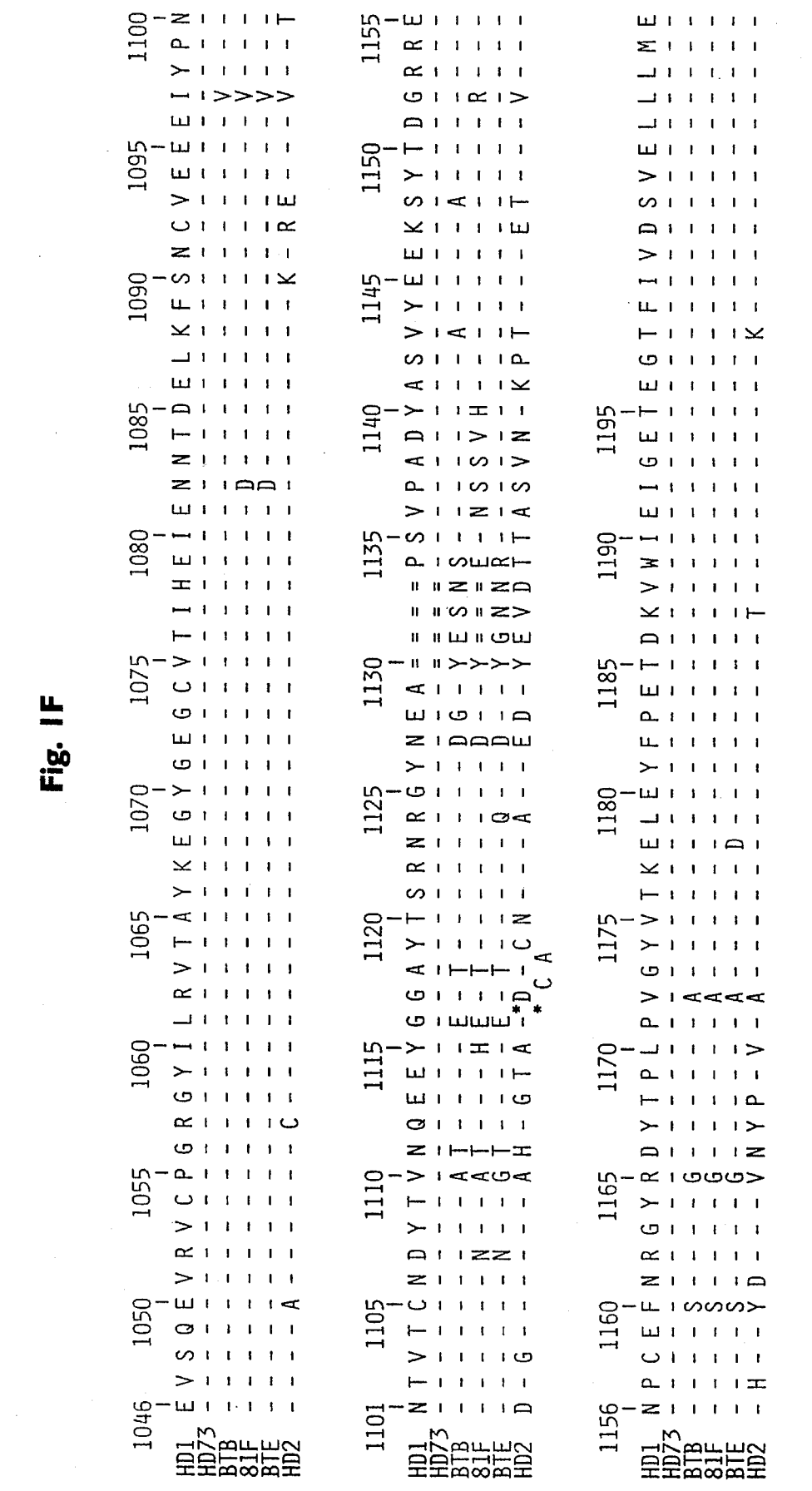

Total cellular DNA partially digested with Sau3A and fractionated by electrophoresis into a mixture of 9–23 Kb fragments on a 0.6% agarose TAE gel was ligated into LAMBDA DASH™ (Stratagene). The packaged phage were plated out with P2392 *E. coli* cells (Stratagene) at a high titer and screened using the radiolabeled synthetic oligonucleotide supra as a nucleic acid hybridization probe. Hybridizing plaques were rescreened at a lower plaque density. A purified hybridizing plaque was used to infect P2392 *E. coli* cells in liquid culture for preparation of phage for DNA isolation. DNA was isolated by standard procedures. Preparative amounts of recombinant phage DNA were digested with SalI (to release the inserted DNA from lambda arms) and separated by electrophoresis on a 0.6% Agarose-TAE gel. The large fragments (electroeluted and concentrated as described above) were ligated to an XhoI digested and phosphatased BLUESCRIPT™ plasmid. The ligation was transformed into *E. coli* DH5(α) competent cells (BRL) and plated on LB agar containing ampicillin, isopropyl-(β)-D-thiogalactoside (IPFG) and 5-bromo-4-chloro-3-indolyl-(β)-D-galactoside (XGAL). White colonies (with insertions in the (β)-galactosidase gene of pBluescript) were subjected to standard miniprep procedures to isolate the plasmid, designated pMl,43-24. The full length toxin gene was sequenced by using oligonucleotide primers made to the "4.3 Kb class" toxin gene and by "walking" with primers made to the sequence of PS81F. Data analysis comparing the deduced PS81F amino acid sequence to the sequences of five other endotoxins shows PS81F to be unique (FIG. 1).

The plasmid pM1,43-24 contains about 18 Kb of PS81F DNA including the 3.518 Kb which codes for the 133,266 dalton endotoxin. The plasmid was reduced in size by cutting out approximately 13 Kb of non-coding DNA, ligating the ends, transforming DH5(α) and plating on LB agar containing ampicillin. The resulting colonies were analyzed by standard miniprep procedures to isolate plasmids that were reduced in size. The desired plasmid, pMYC386, contains the coding sequence of the PS81F toxin gene, which could be excised as an SaeI to ApaI 4.5 Kb fragment.

The above cloning procedures were conducted using standard procedures unless otherwise noted.

The various methods employed in the preparation of the plasmids and transformation of host organisms are well known in the art. Also, methods for the use of lambda bacteriophage as a cloning vehicle, i.e., the preparation of lambda DNA, in vitro packaging, and transfection of recombinant DNA, are well known in the art. These procedures are all described in Maniails, T., Fritsch, E. F., and Sambrook, J. (1982) *Molecular Cloning: A Laboratory Manual*, Cold Spring Harbor Laboratory, New York. Thus, it is within the skill of those in the genetic engineering art to extract DNA from microbial cells, perform restriction enzyme digestions, electrophorese DNA fragments, taft and anneal plasmid and insert DNA, ligate DNA, transform cells, prepare plasmid DNA, electrophorese proteins, and sequence DNA.

The restriction enzymes disclosed herein can be purchased from Bethesda Research Laboratories, Gaithersburg, Md., or New England Biolabs, Beverly, Mass. The enzymes are used according to the instructions provided by the supplier.

Plasmid pMYC386 containing the *B.t.* toxin gene, can be removed from the transformed host microbe by use of standard well-known procedures. For example, *E. coli* NRRL B-18423 can be subjected to cleared lysate isopycnic density gradient procedures, and the like, to recover pMYC386.

EXAMPLE 6

Insertion of Toxin Gene Into Plants

The novel gene coding for the novel antiprotozoan toxin, as disclosed herein, can be inserted into plant cells using the Ti plasmid from *Agrobacter tumefaciens*. Plant cells can then be caused to regenerate into plants (Zambryski, P., Joos, H., Gentelto, C., Leemans, J., Van Móntague, M. and Schell, J [1983] Cell 32:1033–1043). A particularly useful vector in this regard is pEND4K (Klee, H. J., Yanofsky, M. F. and Nester, E. W. [1985] Bio/Technology 3:637–642). This plasmid can replicate both in plant cells and in bacteria and has multiple cloning sites for passenger genes. The toxin gene, for example, can be inserted into the BamHI site of pEND4K, propagated in *E. coli*, and transformed into appropriate plant cells.

EXAMPLE 7

Cloning of Novel *B. thuringiensis* Gene Into Baculoviruses

The novel gene of the invention can be cloned into baculoviruses such as *Autographa californica* nuclear polyhedrosis virus (AcNPV). Plasmids can be constructed that contain the AcNPV genome cloned into a commercial cloning vector such as pUC8. The AcNPV genome is modified so that the coding region of the polyhedrin gene is removed and a unique cloning site for a passenger gene is placed directly behind the polyhedrin promoter. Examples of such vectors are pGP-B6874, described by Pennock et al. (Pennook, G. D., Shoemaker, C. and Miller, L. K. [1984] Mol. Cell. Biol. 4:399–406), and pAC380, described by Smith et al. (Smith, G. E., Summers, M. D. and Fraser, M. J. [1983] Mol Cell. Biol. 3:2156–2165). The gene coding for the novel protein tom of the invention can be modified with BamHI linkers at appropriate regions both upstream and downstream from the coding region and inserted into the passenger site of one of the AcNPV vectors.

As disclosed previously, the nucleotide sequence encoding the novel *B.t.* toxin gene is shown in SEQ ID NO. 1. The deduced amino acid sequence is shown in SEQ ID NO. 2.

It is well known in the art that the amino acid sequence of a protein is determined by the nucleotide sequence of the DNA. Because of the redundancy of the genetic code, i.e., more than one coding nucleotide triplet (codon) can be used for most of the amino acids used to make proteins, different nucleotide sequences can code for a particular amino acid. Thus, the genetic code can be depicted as follows:

| Phenylalanine (Phe) | TTK | Histidine (His) | CAK |
| Leucine (Leu) | XTY | Glutamine (Gln) | CAJ |
| Isoleucine (Ile) | ATM | Asparagine (Asn) | AAK |
| Methionine (Met) | ATG | Lysine (Lys) | AAJ |
| Valine (Val) | GTL | Aspartic acid (Asp) | GAK |
| Serine (Ser) | QRS | Glutamic acid (Glu) | GAJ |
| Proline (Pro) | CCL | Cysteine (Cys) | TGK |
| Threonine (Thr) | ACL | Tryptophan (Trp) | TGG |
| Alanine (Ala) | GCL | Arginine (Arg) | WGZ |
| Tyrosine (Tyr) | TAK | Glycine (Gly) | GGL |
| Termination signal | TAJ | | |

Key: Each 3-letter deoxynucleotide triplet corresponds to a trinucleotide of mRNA, having a 5'-end on the left and a 3'-end on the right. All DNA sequences given herein are those of the strand whose sequence correspond to the mRNA sequence, with thymine substituted for uracil. The letters stand for the purine or pyrimidine bases forming the deoxynucleotide sequence.

A=adenine

G=guanine

C=cytosine

T=thymine

X=T or C if Y is A or G

X=C if Y is C or T

Y=A, G, C or T if X is C

Y=A or G if X is T

W=C or A if Z is A or G

W=C if Z is C or T

Z=A, G, C or T if W is C

Z=A or G if W is A

QR=TC if S is A, G, C or T; alternatively QR=AG if S is T or C

J=A or G

K=T or C

L=A, T, C or G

M=A, C or T

The above shows that the novel amino acid sequence of the *B.t.* toxin can be prepared by equivalent nucleotide sequences encoding the same amino acid sequence of the protein. Accordingly, the subject invention includes such equivalent nucleotide sequences. In addition it has been shown that proteins of identified structure and function may be constructed by changing the amino acid sequence if such changes do not alter the protein secondary structure (Kaiser, E. T. and Kezdy, F. J. [1984] Science 223:249–255). Thus, the subject invention includes mutants of the amino acid sequence depicted herein which do not alter the protein secondary structure, or if the structure is altered, the biological activity is retained to some degree.

We claim:

1. A process for treating a mammalian host infected with a protozoan pest of the genus Giardia which comprises administering to said host an effective protozoan inhibiting mount of a *Bacillus thuringiensis* microbe having substantially the antiprotozoan activity of *Bacillus thuringiensis* PS81F, the inclusion bodies from said microbe, or a purified protein toxin having the amino acid sequence shown in SEQ ID NO. 2.

2. The process, according to claim 1, wherein said protozoan is *Giardia lamblia* and said host is a human.

3. The process, according to claim 2, wherein about 1 to about 20 g of *Bacillus thuringiensis* microbe having substantially the antiprotozoan activity of *Bacillus thuringiensis* PS81F, the protein inclusion bodies from said microbe, or a purified toxin having the amino acid sequence shown in SEQ ID NO. 2.

4. The process, according to claim 1, wherein said microbe, inclusion bodies or toxin is administered orally to said host.

5. A process for treating a mammalian host infected with the protozoan *Giardia lamblia* which comprises orally administering to said host an effective protozoan inhibiting amount of a *Bacillus thuringiensis* microbe having substantially the activity of *Bacillus thuringiensis* PS81F, the inclusion bodies from said microbe, or a purified protein toxin having the amino acid sequence shown in SEQ ID NO. 2.

* * * * *

UNITED STATES PATENT AND TRADEMARK OFFICE
CERTIFICATE OF CORRECTION

PATENT NO. : 5,468,483    Page 1 of 2
DATED : Nov. 21, 1995
INVENTOR(S) : Mark Thompson, et al It is certified that error appears in the above-indentified patent and that said Letters Patent is hereby corrected as shown below:

Column 1, line 58: "(Hofte; H.," should read --(Hofte, H.,--
Column 2, line 52: "_____" should read -- -- -- -- -- -- -- --
Column 2, line 53: "_____" should read --======--
Column 4, line 4: "peanut off, cotton seed off" should read --peanut oil, cotton seed oil--
Column 4, line 7: "use& The" should read --used. The--
Column 4, line 31: "$B.t.$: isolate" should read --$B.t.$ isolate--
Column 7, line 32-33: "$MnSO_4$ - $3H_2O$" should read --$MnSO_4$ - $H_2O$--
Column 9, line 61: "(IPFG)" should read --(IPTG)--
Column 10, line 23: "Maniails," should read --Maniatis--
Column 10, line 28: "taft" should read --tail--
Column 11, line 12: "tom" should read --toxin--
Column 11, line 19: "an" should read --art--

UNITED STATES PATENT AND TRADEMARK OFFICE
CERTIFICATE OF CORRECTION

PATENT NO. : 5,468,483
DATED : November 21, 1995
INVENTOR(S) : Mark Thompson, et al It is certified that error appears in the above-indentified patent and that said Letters Patent is hereby corrected as shown below:

Column 29, line 40: "mount" should read --amount--
Column 30, line 37: "SEQ ID NO. 2." should read --SEQ ID NO. 2, are administered to the human host.--

Signed and Sealed this

Twenty-third Day of April, 1996

Attest:

BRUCE LEHMAN

Attesting Officer        Commissioner of Patents and Trademarks

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 3513 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:1:

```
ATGGAGATAG  TGAATAATCA  GAATCAATGC  GTGCCTTATA  ATTGTTTAAA  TAATCCTGAA     60

AATGAGATAT  TAGATATTGA  AAGGTCAAAT  AGTACTGTAG  CAACAAACAT  CGCCTTGGAG    120

ATTAGTCGTC  TGCTCGCTTC  CGCAACTCCA  ATAGGGGGGA  TTTTATTAGG  ATTGTTTGAT    180

GCAATATGGG  GGTCTATAGG  CCCTTCACAA  TGGGATTTAT  TTTTAGAGCA  AATTGAGCTA    240

TTGATTGACC  AAAAAAATAGA  GGAATTCGCT  AGAAACCAGG  CAATTTCTAG  ATTAGAAGGG    300
```

| | | | | | | |
|---|---|---|---|---|---|---|
| ATAAGCAGTC | TGTACGGAAT | TTATACAGAA | GCTTTTAGAG | AGTGGGAAGC | AGATCCTACT | 360 |
| AATCCAGCAT | TAAAAGAAGA | GATGCGTACT | CAATTAATG | ACATGAACAG | TATTCTTGTA | 420 |
| ACAGCTATTC | CTCTTTTTTC | AGTTCAAAAT | TATCAAGTCC | CATTTTATC | AGTATATGTT | 480 |
| CAAGCTGCAA | ATTTACATTT | ATCGGTTTTG | AGAGATGTTT | CAGTGTTTGG | GCAGGCTTGG | 540 |
| GGATTTGATA | TAGCAACAAT | AAATAGTCGT | TATAATGATC | TGACTAGACT | TATTCCTATA | 600 |
| TATACAGATT | ATGCTGTACG | CTGGTACAAT | ACGGGATTAG | ATCGCTTACC | ACGAACTGGT | 660 |
| GGGCTGCGAA | ACTGGGCAAG | ATTTAATCAG | TTTAGAAGAG | AGTAACAAT | ATCAGTATTA | 720 |
| GATATTATTT | CTTTTTTCAG | AAATTACGAT | TCTAGATTAT | ATCCAATTCC | AACAAGCTCC | 780 |
| CAATTAACGC | GGGAAGTATA | TACAGATCCG | GTAATTAATA | TAACTGACTA | TAGAGTTGGC | 840 |
| CCCAGCTTCG | AGAATATTGA | GAACTCAGCC | ATTAGAAGCC | CCCACCTTAT | GGACTTCTTA | 900 |
| AATAATTTGA | CCATTGATAC | GGATTTGATT | AGAGGTGTTC | ACTATTGGGC | AGGGCATCGT | 960 |
| GTAACTTCTC | ATTTTACAGG | TAGTTCTCAA | GTGATAACAA | CCCCTCAATA | TGGGATAACC | 1020 |
| GCAAATGCGG | AACCAAGACG | AACTATTGCT | CCTAGTACTT | TTCCAGGTCT | TAACCTATTT | 1080 |
| TATAGAACAT | TATCAAATCC | TTTCTTCCGA | AGATCAGAAA | ATATTACTCC | TACCTTAGGG | 1140 |
| ATAAATGTAG | TACAGGGAGT | AGGGTTCATT | CAACCAAATA | ATGCTGAAGT | TCTATATAGA | 1200 |
| AGTAGGGGGA | CAGTAGATTC | TCTTAATGAG | TTACCAATTG | ATGGTGAGAA | TTCATTAGTT | 1260 |
| GGATATAGTC | ATCGATTAAG | TCATGTTACA | CTAACCAGGT | CGTTATATAA | TACTAATATA | 1320 |
| ACTAGCCTGC | CAACATTTGT | TTGGACACAT | CACAGTGCTA | CTAATACAAA | TACAATTAAT | 1380 |
| CCAGATATTA | TTACACAAAT | ACCTTTAGTG | AAAGGATTTA | GACTTGGTGG | TGGCACCTCT | 1440 |
| GTCATTAAAG | GACCAGGATT | TACAGGAGGG | GATATCCTTC | GAAGAAATAC | CATTGGTGAG | 1500 |
| TTTGTGTCTT | TACAAGTCAA | TATTAACTCA | CCAATTACCC | AAAGATACCG | TTTAAGATTT | 1560 |
| CGTTATGCTT | CCAGTAGGGA | TGCACGAATT | ACTGTAGCGA | TAGGAGGACA | AATTAGAGTA | 1620 |
| GATATGACCC | TTGAAAAAAC | CATGGAAATT | GGGGAGAGCT | TAACATCTAG | AACATTTAGC | 1680 |
| TATACCAATT | TTAGTAATCC | TTTTTCATTT | AGGGCTAATC | CAGATATAAT | TAGAATAGCT | 1740 |
| GAAGAACTTC | CTATTCGTGG | TGGTGAGCTT | TATATAGATA | AAATTGAACT | TATTCTAGCA | 1800 |
| GATGCAACAT | TTGAAGAAGA | ATATGATTTG | GAAAGAGCAC | AGAAGGCGGT | GAATGCCCTG | 1860 |
| TTTACTTCTA | CAAATCAACT | AGGGCTAAAA | ACAGATGTGA | CGGATTATCA | TATTGATCAA | 1920 |
| GTTTCCAATT | TAGTTGAGTG | TTTATCGGAT | GAATTTGTC | TGGATGAAAA | GAGAGAATTA | 1980 |
| TCCGAGAAAG | TCAAACATGC | GAAGCGACTC | AGTGATGAAC | GGAATTTACT | TCAAGATCCA | 2040 |
| AACTTCAGAG | GGATCAATAG | GCAACCAGAC | CGTGGCTGGA | GAGGAAGCAC | GGATATTACT | 2100 |
| ATCCAAGGTG | GAGATGACGT | ATTCAAAGAG | AATTACGTCA | CATTACCGGG | TACCTTTGAT | 2160 |
| GAGTGCTATC | CAACGTATTT | ATATCAAAAA | ATAGATGAGT | CGAAGTTAAA | AGCTTATACC | 2220 |
| CGCTATGAAT | TAAGAGGGTA | TATCGAGGAT | AGTCAAGACT | TAGAAATCTA | TTTAATTCGC | 2280 |
| TACAATGCAA | AACACGAGAC | AGTAAACGTG | CCAGGTACGG | GTTCCTTATG | GCCGCTTTCA | 2340 |
| GCCCAAAGTC | CAATCGGAAA | GTGTGGAGAA | CCGAATCGAT | GCGCGCCACA | CCTTGAATGG | 2400 |
| AATCCTAATC | TAGATTGCTC | CTGCAGAGAC | GGGGAAAAAT | GTGCCCATCA | TTCCCATCAT | 2460 |
| TTCTCCTTGG | ACATTGATGT | TGGATGTACA | GACTTAAATG | AGGACTTAGG | TGTATGGGTG | 2520 |
| ATATTCAAGA | TTAAGACACA | AGATGGCTAT | GCAAGACTAG | GAAATCTAGA | GTTTCTCGAA | 2580 |
| GAGAAACCAC | TATTAGGGGA | AGCACTAGCT | CGTGTGAAAA | GAGCGGAGAA | AAAATGGAGA | 2640 |

| | | | | | |
|---|---|---|---|---|---|
| GACAAATGCG | AAAAATTGGA | ATGGGAAACA | AATATTGTTT | ATAAAGAGGC | AAAAGAATCT | 2700 |
| GTAGATGCTT | TATTTGTAAA | CTCTCAATAT | GATAGATTAC | AAGCGGATAC | GAATATCGCG | 2760 |
| ATGATTCATG | CGGCAGATAA | ACGCGTTCAT | AGCATTCGAG | AAGCGTATCT | GCCAGAGCTG | 2820 |
| TCTGTGATTC | CGGGTGTCAA | TGCGGCTATT | TTTGAAGAAT | TAGAAGGGCG | TATTTTCACT | 2880 |
| GCATTCTCCC | TATATGATGC | GAGAAATGTC | ATTAAAAATG | GCGATTTCAA | TAATGGCTTA | 2940 |
| TCATGCTGGA | ACGTGAAAGG | CATGTAGAT | GTAGAAGAAC | AGAACAACCA | TCGTTCGGTC | 3000 |
| CTTGTTGTTC | CAGAATGGGA | AGCAGAAGTG | TCACAAGAAG | TTCGTGTTTG | TCCGGGTCGT | 3060 |
| GGCTATATCC | TTCGTGTTAC | AGCGTACAAA | GAGGGATATG | GAGAGGGCTG | TGTAACGATT | 3120 |
| CATGAGATCG | AAGACAATAC | AGACGAACTG | AAATTCAGCA | ACTGTGTAGA | AGAGGAAGTA | 3180 |
| TATCCAAACA | ACACGGTAAC | GTGTAATAAT | TATACTGCGA | CTCAAGAAGA | ACATGAGGGT | 3240 |
| ACGTACACTT | CCCGTAATCG | AGGATATGAC | GAAGCCTATG | AAAGCAATTC | TTCTGTACAT | 3300 |
| GCGTCAGTCT | ATGAAGAAAA | ATCGTATACA | GATAGACGAA | GAGAGAATCC | TTGTGAATCT | 3360 |
| AACAGAGGAT | ATGGGGATTA | CACACCACTA | CCAGCTGGCT | ATGTGACAAA | AGAATTAGAG | 3420 |
| TACTTCCCAG | AAACCGATAA | GGTATGGATT | GAGATCGGAG | AAACGGAAGG | AACATTCATC | 3480 |
| GTGGACAGCG | TGGAATTACT | TCTTATGGAG | GAA | | | 3513 |

( 2 ) INFORMATION FOR SEQ ID NO:2:

( i ) SEQUENCE CHARACTERISTICS:
        ( A ) LENGTH: 1171 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Glu Ile Val Asn Asn Gln Asn Gln Cys Val Pro Tyr Asn Cys Leu
 1               5                  10                  15

Asn Asn Pro Glu Asn Glu Ile Leu Asp Ile Glu Arg Ser Asn Ser Thr
            20                  25                  30

Val Ala Thr Asn Ile Ala Leu Glu Ile Ser Arg Leu Leu Ala Ser Ala
        35                  40                  45

Thr Pro Ile Gly Gly Ile Leu Gly Leu Phe Asp Ala Ile Trp Gly
    50                  55                  60

Ser Ile Gly Pro Ser Gln Trp Asp Leu Phe Leu Glu Gln Ile Glu Leu
65                  70                  75                  80

Leu Ile Asp Gln Lys Ile Glu Glu Phe Ala Arg Asn Gln Ala Ile Ser
                85                  90                  95

Arg Leu Glu Gly Ile Ser Ser Leu Tyr Gly Ile Tyr Thr Glu Ala Phe
            100                 105                 110

Arg Glu Trp Glu Ala Asp Pro Thr Asn Pro Ala Leu Lys Glu Glu Met
        115                 120                 125

Arg Thr Gln Phe Asn Asp Met Asn Ser Ile Leu Val Thr Ala Ile Pro
    130                 135                 140

Leu Phe Ser Val Gln Asn Tyr Gln Val Pro Phe Leu Ser Val Tyr Val
145                 150                 155                 160

Gln Ala Ala Asn Leu His Leu Ser Val Leu Arg Asp Val Ser Val Phe
                165                 170                 175

Gly Gln Ala Trp Gly Phe Asp Ile Ala Thr Ile Asn Ser Arg Tyr Asn
            180                 185                 190

Asp Leu Thr Arg Leu Ile Pro Ile Tyr Thr Asp Tyr Ala Val Arg Trp
```

-continued

|  | 195 |  |  |  |  | 200 |  |  |  |  | 205 |  |  |  |
|---|---|---|---|---|---|---|---|---|---|---|---|---|---|---|
| Tyr | Asn 210 | Thr | Gly | Leu | Asp | Arg 215 | Leu | Pro | Arg | Thr | Gly 220 | Gly | Leu | Arg | Asn |
| Trp 225 | Ala | Arg | Phe | Asn | Gln 230 | Phe | Arg | Arg | Glu | Leu 235 | Thr | Ile | Ser | Val | Leu 240 |
| Asp | Ile | Ile | Ser | Phe 245 | Phe | Arg | Asn | Tyr | Asp 250 | Ser | Arg | Leu | Tyr | Pro 255 | Ile |
| Pro | Thr | Ser | Ser 260 | Gln | Leu | Thr | Arg | Glu 265 | Val | Tyr | Thr | Asp | Pro 270 | Val | Ile |
| Asn | Ile | Thr 275 | Asp | Tyr | Arg | Val | Gly 280 | Pro | Ser | Phe | Glu | Asn 285 | Ile | Glu | Asn |
| Ser | Ala 290 | Ile | Arg | Ser | Pro | His 295 | Leu | Met | Asp | Phe | Leu 300 | Asn | Asn | Leu | Thr |
| Ile 305 | Asp | Thr | Asp | Leu | Ile 310 | Arg | Gly | Val | His | Tyr 315 | Trp | Ala | Gly | His | Arg 320 |
| Val | Thr | Ser | His | Phe 325 | Thr | Gly | Ser | Ser | Gln 330 | Val | Ile | Thr | Thr | Pro 335 | Gln |
| Tyr | Gly | Ile | Thr 340 | Ala | Asn | Ala | Glu | Pro 345 | Arg | Arg | Thr | Ile | Ala 350 | Pro | Ser |
| Thr | Phe | Pro 355 | Gly | Leu | Asn | Leu | Phe 360 | Tyr | Arg | Thr | Leu | Ser 365 | Asn | Pro | Phe |
| Phe | Arg 370 | Arg | Ser | Glu | Asn | Ile 375 | Thr | Pro | Thr | Leu | Gly 380 | Ile | Asn | Val | Val |
| Gln 385 | Gly | Val | Gly | Phe | Ile 390 | Gln | Pro | Asn | Asn | Ala 395 | Glu | Val | Leu | Tyr | Arg 400 |
| Ser | Arg | Gly | Thr | Val 405 | Asp | Ser | Leu | Asn | Glu 410 | Leu | Pro | Ile | Asp | Gly 415 | Glu |
| Asn | Ser | Leu | Val 420 | Gly | Tyr | Ser | His | Arg 425 | Leu | Ser | His | Val | Thr 430 | Leu | Thr |
| Arg | Ser | Leu 435 | Tyr | Asn | Thr | Asn | Ile 440 | Thr | Ser | Leu | Pro | Thr 445 | Phe | Val | Trp |
| Thr | His 450 | His | Ser | Ala | Thr | Asn 455 | Thr | Asn | Thr | Ile | Asn 460 | Pro | Asp | Ile | Ile |
| Thr 465 | Gln | Ile | Pro | Leu | Val 470 | Lys | Gly | Phe | Arg | Leu 475 | Gly | Gly | Gly | Thr | Ser 480 |
| Val | Ile | Lys | Gly | Pro 485 | Gly | Phe | Thr | Gly | Gly 490 | Asp | Ile | Leu | Arg | Arg 495 | Asn |
| Thr | Ile | Gly | Glu 500 | Phe | Val | Ser | Leu | Gln 505 | Val | Asn | Ile | Asn | Ser 510 | Pro | Ile |
| Thr | Gln | Arg 515 | Tyr | Arg | Leu | Arg | Phe 520 | Arg | Tyr | Ala | Ser | Ser 525 | Arg | Asp | Ala |
| Arg | Ile 530 | Thr | Val | Ala | Ile | Gly 535 | Gly | Gln | Ile | Arg | Val 540 | Asp | Met | Thr | Leu |
| Glu 545 | Lys | Thr | Met | Glu | Ile 550 | Gly | Glu | Ser | Leu | Thr 555 | Ser | Arg | Thr | Phe | Ser 560 |
| Tyr | Thr | Asn | Phe | Ser 565 | Asn | Pro | Phe | Ser | Phe 570 | Arg | Ala | Asn | Pro | Asp 575 | Ile |
| Ile | Arg | Ile | Ala 580 | Glu | Glu | Leu | Pro | Ile 585 | Arg | Gly | Gly | Glu | Leu 590 | Tyr | Ile |
| Asp | Lys | Ile 595 | Glu | Leu | Ile | Leu | Ala 600 | Asp | Ala | Thr | Phe | Glu 605 | Glu | Glu | Tyr |
| Asp | Leu 610 | Glu | Arg | Ala | Gln | Lys 615 | Ala | Val | Asn | Ala | Leu 620 | Phe | Thr | Ser | Thr |

-continued

| | | | | | | | | | | | | | | |
|---|---|---|---|---|---|---|---|---|---|---|---|---|---|---|
| Asn | Gln | Leu | Gly | Leu | Lys | Thr | Asp | Val | Thr | Asp | Tyr | His | Ile | Asp | Gln |
| 625 | | | | | 630 | | | | 635 | | | | | | 640 |
| Val | Ser | Asn | Leu | Val | Glu | Cys | Leu | Ser | Asp | Glu | Phe | Cys | Leu | Asp | Glu |
| | | | | 645 | | | | | 650 | | | | | 655 | |
| Lys | Arg | Glu | Leu | Ser | Glu | Lys | Val | Lys | His | Ala | Lys | Arg | Leu | Ser | Asp |
| | | | 660 | | | | | 665 | | | | | 670 | | |
| Glu | Arg | Asn | Leu | Leu | Gln | Asp | Pro | Asn | Phe | Arg | Gly | Ile | Asn | Arg | Gln |
| | | 675 | | | | | 680 | | | | | 685 | | | |
| Pro | Asp | Arg | Gly | Trp | Arg | Gly | Ser | Thr | Asp | Ile | Thr | Ile | Gln | Gly | Gly |
| | 690 | | | | | 695 | | | | 700 | | | | | |
| Asp | Asp | Val | Phe | Lys | Glu | Asn | Tyr | Val | Thr | Leu | Pro | Gly | Thr | Phe | Asp |
| 705 | | | | | 710 | | | | | 715 | | | | | 720 |
| Glu | Cys | Tyr | Pro | Thr | Tyr | Leu | Tyr | Gln | Lys | Ile | Asp | Glu | Ser | Lys | Leu |
| | | | | 725 | | | | | 730 | | | | | 735 | |
| Lys | Ala | Tyr | Thr | Arg | Tyr | Glu | Leu | Arg | Gly | Tyr | Ile | Glu | Asp | Ser | Gln |
| | | | 740 | | | | | 745 | | | | | 750 | | |
| Asp | Leu | Glu | Ile | Tyr | Leu | Ile | Arg | Tyr | Asn | Ala | Lys | His | Glu | Thr | Val |
| | | 755 | | | | | 760 | | | | | 765 | | | |
| Asn | Val | Pro | Gly | Thr | Gly | Ser | Leu | Trp | Pro | Leu | Ser | Ala | Gln | Ser | Pro |
| | 770 | | | | | 775 | | | | | 780 | | | | |
| Ile | Gly | Lys | Cys | Gly | Glu | Pro | Asn | Arg | Cys | Ala | Pro | His | Leu | Glu | Trp |
| 785 | | | | | 790 | | | | | 795 | | | | | 800 |
| Asn | Pro | Asn | Leu | Asp | Cys | Ser | Cys | Arg | Asp | Gly | Glu | Lys | Cys | Ala | His |
| | | | | 805 | | | | | 810 | | | | | 815 | |
| His | Ser | His | His | Phe | Ser | Leu | Asp | Ile | Asp | Val | Gly | Cys | Thr | Asp | Leu |
| | | | 820 | | | | | 825 | | | | | 830 | | |
| Asn | Glu | Asp | Leu | Gly | Val | Trp | Val | Ile | Phe | Lys | Ile | Lys | Thr | Gln | Asp |
| | | 835 | | | | | 840 | | | | | 845 | | | |
| Gly | Tyr | Ala | Arg | Leu | Gly | Asn | Leu | Glu | Phe | Leu | Glu | Glu | Lys | Pro | Leu |
| | 850 | | | | | 855 | | | | | 860 | | | | |
| Leu | Gly | Glu | Ala | Leu | Ala | Arg | Val | Lys | Arg | Ala | Glu | Lys | Lys | Trp | Arg |
| 865 | | | | | 870 | | | | | 875 | | | | | 880 |
| Asp | Lys | Cys | Glu | Lys | Leu | Glu | Trp | Glu | Thr | Asn | Ile | Val | Tyr | Lys | Glu |
| | | | | 885 | | | | | 890 | | | | | 895 | |
| Ala | Lys | Glu | Ser | Val | Asp | Ala | Leu | Phe | Val | Asn | Ser | Gln | Tyr | Asp | Arg |
| | | | 900 | | | | | 905 | | | | | 910 | | |
| Leu | Gln | Ala | Asp | Thr | Asn | Ile | Ala | Met | Ile | His | Ala | Ala | Asp | Lys | Arg |
| | | 915 | | | | | 920 | | | | | 925 | | | |
| Val | His | Ser | Ile | Arg | Glu | Ala | Tyr | Leu | Pro | Glu | Leu | Ser | Val | Ile | Pro |
| | 930 | | | | | 935 | | | | | 940 | | | | |
| Gly | Val | Asn | Ala | Ala | Ile | Phe | Glu | Glu | Leu | Glu | Gly | Arg | Ile | Phe | Thr |
| 945 | | | | | 950 | | | | | 955 | | | | | 960 |
| Ala | Phe | Ser | Leu | Tyr | Asp | Ala | Arg | Asn | Val | Ile | Lys | Asn | Gly | Asp | Phe |
| | | | | 965 | | | | | 970 | | | | | 975 | |
| Asn | Asn | Gly | Leu | Ser | Cys | Trp | Asn | Val | Lys | Gly | His | Val | Asp | Val | Glu |
| | | | 980 | | | | | 985 | | | | | 990 | | |
| Glu | Gln | Asn | Asn | His | Arg | Ser | Val | Leu | Val | Val | Pro | Glu | Trp | Glu | Ala |
| | | 995 | | | | | 1000 | | | | | 1005 | | | |
| Glu | Val | Ser | Gln | Glu | Val | Arg | Val | Cys | Pro | Gly | Arg | Gly | Tyr | Ile | Leu |
| | | 1010 | | | | | 1015 | | | | | 1020 | | | |
| Arg | Val | Thr | Ala | Tyr | Lys | Glu | Gly | Tyr | Gly | Glu | Gly | Cys | Val | Thr | Ile |
| 1025 | | | | | 1030 | | | | | 1035 | | | | | 1040 |

-continued

| His | Glu | Ile | Glu | Asp | Asn | Thr | Asp | Glu | Leu | Lys | Phe | Ser | Asn | Cys | Val |
|     |     |     |     | 1045 |     |     |     | 1050 |     |     |     |     |     | 1055 |     |

| Glu | Glu | Glu | Val | Tyr | Pro | Asn | Asn | Thr | Val | Thr | Cys | Asn | Asn | Tyr | Thr |
|     |     |     |     | 1060 |     |     |     | 1065 |     |     |     |     |     | 1070 |     |

| Ala | Thr | Gln | Glu | Glu | His | Glu | Gly | Thr | Tyr | Thr | Ser | Arg | Asn | Arg | Gly |
|     |     |     |     | 1075 |     |     |     | 1080 |     |     |     |     |     | 1085 |     |

| Tyr | Asp | Glu | Ala | Tyr | Glu | Ser | Asn | Ser | Ser | Val | His | Ala | Ser | Val | Tyr |
|     |     | 1090 |     |     |     |     |     | 1095 |     |     |     | 1100 |     |     |     |

| Glu | Glu | Lys | Ser | Tyr | Thr | Asp | Arg | Arg | Arg | Glu | Asn | Pro | Cys | Glu | Ser |
| 1105 |     |     |     |     | 1110 |     |     |     |     | 1115 |     |     |     |     | 1120 |

| Asn | Arg | Gly | Tyr | Gly | Asp | Tyr | Thr | Pro | Leu | Pro | Ala | Gly | Tyr | Val | Thr |
|     |     |     |     | 1125 |     |     |     | 1130 |     |     |     |     |     | 1135 |     |

| Lys | Glu | Leu | Glu | Tyr | Phe | Pro | Glu | Thr | Asp | Lys | Val | Trp | Ile | Glu | Ile |
|     |     |     |     | 1140 |     |     |     | 1145 |     |     |     |     |     | 1150 |     |

| Gly | Glu | Thr | Glu | Gly | Thr | Phe | Ile | Val | Asp | Ser | Val | Glu | Leu | Leu | Leu |
|     |     |     |     | 1155 |     |     |     | 1160 |     |     |     |     |     | 1165 |     |

| Met | Glu | Glu |
|     |     | 1170 |

(2) INFORMATION FOR SEQ ID NO:3:

(i) SEQUENCE CHARACTERISTICS:
        (A) LENGTH: 3513 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..3513

(xi) SEQUENCE DESCRIPTION: SEQ ID NO:3:

```
ATG GAG ATA GTG AAT AAT CAG AAT CAA TGC GTG CCT TAT AAT TGT TTA        48
Met Glu Ile Val Asn Asn Gln Asn Gln Cys Val Pro Tyr Asn Cys Leu
 1               5                  10                  15

AAT AAT CCT GAA AAT GAG ATA TTA GAT ATT GAA AGG TCA AAT AGT ACT        96
Asn Asn Pro Glu Asn Glu Ile Leu Asp Ile Glu Arg Ser Asn Ser Thr
            20                  25                  30

GTA GCA ACA AAC ATC GCC TTG GAG ATT AGT CGT CTG CTC GCT TCC GCA       144
Val Ala Thr Asn Ile Ala Leu Glu Ile Ser Arg Leu Leu Ala Ser Ala
        35                  40                  45

ACT CCA ATA GGG GGG ATT TTA TTA GGA TTG TTT GAT GCA ATA TGG GGG       192
Thr Pro Ile Gly Gly Ile Leu Leu Gly Leu Phe Asp Ala Ile Trp Gly
    50                  55                  60

TCT ATA GGC CCT TCA CAA TGG GAT TTA TTT TTA GAG CAA ATT GAG CTA       240
Ser Ile Gly Pro Ser Gln Trp Asp Leu Phe Leu Glu Gln Ile Glu Leu
65                  70                  75                  80

TTG ATT GAC CAA AAA ATA GAG GAA TTC GCT AGA AAC CAG GCA ATT TCT       288
Leu Ile Asp Gln Lys Ile Glu Glu Phe Ala Arg Asn Gln Ala Ile Ser
                85                  90                  95

AGA TTA GAA GGG ATA AGC AGT CTG TAC GGA ATT TAT ACA GAA GCT TTT       336
Arg Leu Glu Gly Ile Ser Ser Leu Tyr Gly Ile Tyr Thr Glu Ala Phe
            100                 105                 110

AGA GAG TGG GAA GCA GAT CCT ACT AAT CCA GCA TTA AAA GAA GAG ATG       384
Arg Glu Trp Glu Ala Asp Pro Thr Asn Pro Ala Leu Lys Glu Glu Met
        115                 120                 125

CGT ACT CAA TTT AAT GAC ATG AAC AGT ATT CTT GTA ACA GCT ATT CCT       432
Arg Thr Gln Phe Asn Asp Met Asn Ser Ile Leu Val Thr Ala Ile Pro
    130                 135                 140
```

| | | | | | | | | | | | | | | | | |
|---|---|---|---|---|---|---|---|---|---|---|---|---|---|---|---|---|
| CTT | TTT | TCA | GTT | CAA | AAT | TAT | CAA | GTC | CCA | TTT | TTA | TCA | GTA | TAT | GTT | 480 |
| Leu | Phe | Ser | Val | Gln | Asn | Tyr | Gln | Val | Pro | Phe | Leu | Ser | Val | Tyr | Val | |
| 145 | | | | 150 | | | | | 155 | | | | | | 160 | |
| CAA | GCT | GCA | AAT | TTA | CAT | TTA | TCG | GTT | TTG | AGA | GAT | GTT | TCA | GTG | TTT | 528 |
| Gln | Ala | Ala | Asn | Leu | His | Leu | Ser | Val | Leu | Arg | Asp | Val | Ser | Val | Phe | |
| | | | | 165 | | | | 170 | | | | | 175 | | | |
| GGG | CAG | GCT | TGG | GGA | TTT | GAT | ATA | GCA | ACA | ATA | AAT | AGT | CGT | TAT | AAT | 576 |
| Gly | Gln | Ala | Trp | Gly | Phe | Asp | Ile | Ala | Thr | Ile | Asn | Ser | Arg | Tyr | Asn | |
| | | | 180 | | | | | 185 | | | | | 190 | | | |
| GAT | CTG | ACT | AGA | CTT | ATT | CCT | ATA | TAT | ACA | GAT | TAT | GCT | GTA | CGC | TGG | 624 |
| Asp | Leu | Thr | Arg | Leu | Ile | Pro | Ile | Tyr | Thr | Asp | Tyr | Ala | Val | Arg | Trp | |
| | | 195 | | | | | 200 | | | | | 205 | | | | |
| TAC | AAT | ACG | GGA | TTA | GAT | CGC | TTA | CCA | CGA | ACT | GGT | GGG | CTG | CGA | AAC | 672 |
| Tyr | Asn | Thr | Gly | Leu | Asp | Arg | Leu | Pro | Arg | Thr | Gly | Gly | Leu | Arg | Asn | |
| | 210 | | | | | 215 | | | | | 220 | | | | | |
| TGG | GCA | AGA | TTT | AAT | CAG | TTT | AGA | AGA | GAG | TTA | ACA | ATA | TCA | GTA | TTA | 720 |
| Trp | Ala | Arg | Phe | Asn | Gln | Phe | Arg | Arg | Glu | Leu | Thr | Ile | Ser | Val | Leu | |
| 225 | | | | | 230 | | | | | 235 | | | | | 240 | |
| GAT | ATT | ATT | TCT | TTT | TTC | AGA | AAT | TAC | GAT | TCT | AGA | TTA | TAT | CCA | ATT | 768 |
| Asp | Ile | Ile | Ser | Phe | Phe | Arg | Asn | Tyr | Asp | Ser | Arg | Leu | Tyr | Pro | Ile | |
| | | | | 245 | | | | | 250 | | | | | 255 | | |
| CCA | ACA | AGC | TCC | CAA | TTA | ACG | CGG | GAA | GTA | TAT | ACA | GAT | CCG | GTA | ATT | 816 |
| Pro | Thr | Ser | Ser | Gln | Leu | Thr | Arg | Glu | Val | Tyr | Thr | Asp | Pro | Val | Ile | |
| | | | 260 | | | | | 265 | | | | | 270 | | | |
| AAT | ATA | ACT | GAC | TAT | AGA | GTT | GGC | CCC | AGC | TTC | GAG | AAT | ATT | GAG | AAC | 864 |
| Asn | Ile | Thr | Asp | Tyr | Arg | Val | Gly | Pro | Ser | Phe | Glu | Asn | Ile | Glu | Asn | |
| | | 275 | | | | | 280 | | | | | 285 | | | | |
| TCA | GCC | ATT | AGA | AGC | CCC | CAC | CTT | ATG | GAC | TTC | TTA | AAT | AAT | TTG | ACC | 912 |
| Ser | Ala | Ile | Arg | Ser | Pro | His | Leu | Met | Asp | Phe | Leu | Asn | Asn | Leu | Thr | |
| | 290 | | | | | 295 | | | | | 300 | | | | | |
| ATT | GAT | ACG | GAT | TTG | ATT | AGA | GGT | GTT | CAC | TAT | TGG | GCA | GGG | CAT | CGT | 960 |
| Ile | Asp | Thr | Asp | Leu | Ile | Arg | Gly | Val | His | Tyr | Trp | Ala | Gly | His | Arg | |
| 305 | | | | | 310 | | | | | 315 | | | | | 320 | |
| GTA | ACT | TCT | CAT | TTT | ACA | GGT | AGT | TCT | CAA | GTG | ATA | ACA | ACC | CCT | CAA | 1008 |
| Val | Thr | Ser | His | Phe | Thr | Gly | Ser | Ser | Gln | Val | Ile | Thr | Thr | Pro | Gln | |
| | | | | 325 | | | | | 330 | | | | | 335 | | |
| TAT | GGG | ATA | ACC | GCA | AAT | GCG | GAA | CCA | AGA | CGA | ACT | ATT | GCT | CCT | AGT | 1056 |
| Tyr | Gly | Ile | Thr | Ala | Asn | Ala | Glu | Pro | Arg | Arg | Thr | Ile | Ala | Pro | Ser | |
| | | | 340 | | | | | 345 | | | | | 350 | | | |
| ACT | TTT | CCA | GGT | CTT | AAC | CTA | TTT | TAT | AGA | ACA | TTA | TCA | AAT | CCT | TTC | 1104 |
| Thr | Phe | Pro | Gly | Leu | Asn | Leu | Phe | Tyr | Arg | Thr | Leu | Ser | Asn | Pro | Phe | |
| | | 355 | | | | | 360 | | | | | 365 | | | | |
| TTC | CGA | AGA | TCA | GAA | AAT | ATT | ACT | CCT | ACC | TTA | GGG | ATA | AAT | GTA | GTA | 1152 |
| Phe | Arg | Arg | Ser | Glu | Asn | Ile | Thr | Pro | Thr | Leu | Gly | Ile | Asn | Val | Val | |
| | 370 | | | | | 375 | | | | | 380 | | | | | |
| CAG | GGA | GTA | GGG | TTC | ATT | CAA | CCA | AAT | AAT | GCT | GAA | GTT | CTA | TAT | AGA | 1200 |
| Gln | Gly | Val | Gly | Phe | Ile | Gln | Pro | Asn | Asn | Ala | Glu | Val | Leu | Tyr | Arg | |
| 385 | | | | | 390 | | | | | 395 | | | | | 400 | |
| AGT | AGG | GGG | ACA | GTA | GAT | TCT | CTT | AAT | GAG | TTA | CCA | ATT | GAT | GGT | GAG | 1248 |
| Ser | Arg | Gly | Thr | Val | Asp | Ser | Leu | Asn | Glu | Leu | Pro | Ile | Asp | Gly | Glu | |
| | | | | 405 | | | | | 410 | | | | | 415 | | |
| AAT | TCA | TTA | GTT | GGA | TAT | AGT | CAT | CGA | TTA | AGT | CAT | GTT | ACA | CTA | ACC | 1296 |
| Asn | Ser | Leu | Val | Gly | Tyr | Ser | His | Arg | Leu | Ser | His | Val | Thr | Leu | Thr | |
| | | | 420 | | | | | 425 | | | | | 430 | | | |
| AGG | TCG | TTA | TAT | AAT | ACT | AAT | ATA | ACT | AGC | CTG | CCA | ACA | TTT | GTT | TGG | 1344 |
| Arg | Ser | Leu | Tyr | Asn | Thr | Asn | Ile | Thr | Ser | Leu | Pro | Thr | Phe | Val | Trp | |
| | | 435 | | | | | 440 | | | | | 445 | | | | |
| ACA | CAT | CAC | AGT | GCT | ACT | AAT | ACA | AAT | ACA | ATT | AAT | CCA | GAT | ATT | ATT | 1392 |
| Thr | His | His | Ser | Ala | Thr | Asn | Thr | Asn | Thr | Ile | Asn | Pro | Asp | Ile | Ile | |

-continued

|     |     |     |     |     |     |     |     |     |     |     |     |     |     |     |     |      |
|---|---|---|---|---|---|---|---|---|---|---|---|---|---|---|---|---|
| ACA | CAA | ATA | CCT | TTA | GTG | AAA | GGA | TTT | AGA | CTT | GGT | GGT | GGC | ACC | TCT | 1440 |
| Thr | Gln | Ile | Pro | Leu | Val | Lys | Gly | Phe | Arg | Leu | Gly | Gly | Gly | Thr | Ser |      |
| 465 |     |     |     |     | 470 |     |     |     |     | 475 |     |     |     |     | 480 |      |
| GTC | ATT | AAA | GGA | CCA | GGA | TTT | ACA | GGA | GGG | GAT | ATC | CTT | CGA | AGA | AAT | 1488 |
| Val | Ile | Lys | Gly | Pro | Gly | Phe | Thr | Gly | Gly | Asp | Ile | Leu | Arg | Arg | Asn |      |
|     |     |     |     | 485 |     |     |     |     | 490 |     |     |     |     | 495 |     |      |
| ACC | ATT | GGT | GAG | TTT | GTG | TCT | TTA | CAA | GTC | AAT | ATT | AAC | TCA | CCA | ATT | 1536 |
| Thr | Ile | Gly | Glu | Phe | Val | Ser | Leu | Gln | Val | Asn | Ile | Asn | Ser | Pro | Ile |      |
|     |     |     | 500 |     |     |     |     | 505 |     |     |     |     | 510 |     |     |      |
| ACC | CAA | AGA | TAC | CGT | TTA | AGA | TTT | CGT | TAT | GCT | TCC | AGT | AGG | GAT | GCA | 1584 |
| Thr | Gln | Arg | Tyr | Arg | Leu | Arg | Phe | Arg | Tyr | Ala | Ser | Ser | Arg | Asp | Ala |      |
|     |     | 515 |     |     |     |     | 520 |     |     |     |     | 525 |     |     |     |      |
| CGA | ATT | ACT | GTA | GCG | ATA | GGA | GGA | CAA | ATT | AGA | GTA | GAT | ATG | ACC | CTT | 1632 |
| Arg | Ile | Thr | Val | Ala | Ile | Gly | Gly | Gln | Ile | Arg | Val | Asp | Met | Thr | Leu |      |
|     | 530 |     |     |     |     | 535 |     |     |     |     | 540 |     |     |     |     |      |
| GAA | AAA | ACC | ATG | GAA | ATT | GGG | GAG | AGC | TTA | ACA | TCT | AGA | ACA | TTT | AGC | 1680 |
| Glu | Lys | Thr | Met | Glu | Ile | Gly | Glu | Ser | Leu | Thr | Ser | Arg | Thr | Phe | Ser |      |
| 545 |     |     |     |     | 550 |     |     |     |     | 555 |     |     |     |     | 560 |      |
| TAT | ACC | AAT | TTT | AGT | AAT | CCT | TTT | TCA | TTT | AGG | GCT | AAT | CCA | GAT | ATA | 1728 |
| Tyr | Thr | Asn | Phe | Ser | Asn | Pro | Phe | Ser | Phe | Arg | Ala | Asn | Pro | Asp | Ile |      |
|     |     |     |     | 565 |     |     |     |     | 570 |     |     |     |     | 575 |     |      |
| ATT | AGA | ATA | GCT | GAA | GAA | CTT | CCT | ATT | CGT | GGT | GGT | GAG | CTT | TAT | ATA | 1776 |
| Ile | Arg | Ile | Ala | Glu | Glu | Leu | Pro | Ile | Arg | Gly | Gly | Glu | Leu | Tyr | Ile |      |
|     |     |     | 580 |     |     |     |     | 585 |     |     |     |     | 590 |     |     |      |
| GAT | AAA | ATT | GAA | CTT | ATT | CTA | GCA | GAT | GCA | ACA | TTT | GAA | GAA | GAA | TAT | 1824 |
| Asp | Lys | Ile | Glu | Leu | Ile | Leu | Ala | Asp | Ala | Thr | Phe | Glu | Glu | Glu | Tyr |      |
|     |     | 595 |     |     |     |     | 600 |     |     |     |     | 605 |     |     |     |      |
| GAT | TTG | GAA | AGA | GCA | CAG | AAG | GCG | GTG | AAT | GCC | CTG | TTT | ACT | TCT | ACA | 1872 |
| Asp | Leu | Glu | Arg | Ala | Gln | Lys | Ala | Val | Asn | Ala | Leu | Phe | Thr | Ser | Thr |      |
|     | 610 |     |     |     |     | 615 |     |     |     |     | 620 |     |     |     |     |      |
| AAT | CAA | CTA | GGG | CTA | AAA | ACA | GAT | GTG | ACG | GAT | TAT | CAT | ATT | GAT | CAA | 1920 |
| Asn | Gln | Leu | Gly | Leu | Lys | Thr | Asp | Val | Thr | Asp | Tyr | His | Ile | Asp | Gln |      |
| 625 |     |     |     |     | 630 |     |     |     |     | 635 |     |     |     |     | 640 |      |
| GTT | TCC | AAT | TTA | GTT | GAG | TGT | TTA | TCG | GAT | GAA | TTT | TGT | CTG | GAT | GAA | 1968 |
| Val | Ser | Asn | Leu | Val | Glu | Cys | Leu | Ser | Asp | Glu | Phe | Cys | Leu | Asp | Glu |      |
|     |     |     |     | 645 |     |     |     |     | 650 |     |     |     |     | 655 |     |      |
| AAG | AGA | GAA | TTA | TCC | GAG | AAA | GTC | AAA | CAT | GCG | AAG | CGA | CTC | AGT | GAT | 2016 |
| Lys | Arg | Glu | Leu | Ser | Glu | Lys | Val | Lys | His | Ala | Lys | Arg | Leu | Ser | Asp |      |
|     |     |     | 660 |     |     |     |     | 665 |     |     |     |     | 670 |     |     |      |
| GAA | CGG | AAT | TTA | CTT | CAA | GAT | CCA | AAC | TTC | AGA | GGG | ATC | AAT | AGG | CAA | 2064 |
| Glu | Arg | Asn | Leu | Leu | Gln | Asp | Pro | Asn | Phe | Arg | Gly | Ile | Asn | Arg | Gln |      |
|     |     | 675 |     |     |     |     | 680 |     |     |     |     | 685 |     |     |     |      |
| CCA | GAC | CGT | GGC | TGG | AGA | GGA | AGC | ACG | GAT | ATT | ACT | ATC | CAA | GGT | GGA | 2112 |
| Pro | Asp | Arg | Gly | Trp | Arg | Gly | Ser | Thr | Asp | Ile | Thr | Ile | Gln | Gly | Gly |      |
| 690 |     |     |     |     | 695 |     |     |     |     | 700 |     |     |     |     |     |      |
| GAT | GAC | GTA | TTC | AAA | GAG | AAT | TAC | GTC | ACA | TTA | CCG | GGT | ACC | TTT | GAT | 2160 |
| Asp | Asp | Val | Phe | Lys | Glu | Asn | Tyr | Val | Thr | Leu | Pro | Gly | Thr | Phe | Asp |      |
| 705 |     |     |     |     | 710 |     |     |     |     | 715 |     |     |     |     | 720 |      |
| GAG | TGC | TAT | CCA | ACG | TAT | TTA | TAT | CAA | AAA | ATA | GAT | GAG | TCG | AAG | TTA | 2208 |
| Glu | Cys | Tyr | Pro | Thr | Tyr | Leu | Tyr | Gln | Lys | Ile | Asp | Glu | Ser | Lys | Leu |      |
|     |     |     |     | 725 |     |     |     |     | 730 |     |     |     |     | 735 |     |      |
| AAA | GCT | TAT | ACC | CGC | TAT | GAA | TTA | AGA | GGG | TAT | ATC | GAG | GAT | AGT | CAA | 2256 |
| Lys | Ala | Tyr | Thr | Arg | Tyr | Glu | Leu | Arg | Gly | Tyr | Ile | Glu | Asp | Ser | Gln |      |
|     |     |     | 740 |     |     |     |     | 745 |     |     |     |     | 750 |     |     |      |
| GAC | TTA | GAA | ATC | TAT | TTA | ATT | CGC | TAC | AAT | GCA | AAA | CAC | GAG | ACA | GTA | 2304 |
| Asp | Leu | Glu | Ile | Tyr | Leu | Ile | Arg | Tyr | Asn | Ala | Lys | His | Glu | Thr | Val |      |
|     |     | 755 |     |     |     |     | 760 |     |     |     |     | 765 |     |     |     |      |
| AAC | GTG | CCA | GGT | ACG | GGT | TCC | TTA | TGG | CCG | CTT | TCA | GCC | CAA | AGT | CCA | 2352 |

```
              Asn  Val  Pro  Gly  Thr  Gly  Ser  Leu  Trp  Pro  Leu  Ser  Ala  Gln  Ser  Pro
                   770                      775                 780

ATC  GGA  AAG  TGT  GGA  GAA  CCG  AAT  CGA  TGC  GCG  CCA  CAC  CTT  GAA  TGG                 2400
Ile  Gly  Lys  Cys  Gly  Glu  Pro  Asn  Arg  Cys  Ala  Pro  His  Leu  Glu  Trp
785                      790                      795                      800

AAT  CCT  AAT  CTA  GAT  TGC  TCC  TGC  AGA  GAC  GGG  GAA  AAA  TGT  GCC  CAT                 2448
Asn  Pro  Asn  Leu  Asp  Cys  Ser  Cys  Arg  Asp  Gly  Glu  Lys  Cys  Ala  His
                    805                      810                      815

CAT  TCC  CAT  CAT  TTC  TCC  TTG  GAC  ATT  GAT  GTT  GGA  TGT  ACA  GAC  TTA                 2496
His  Ser  His  His  Phe  Ser  Leu  Asp  Ile  Asp  Val  Gly  Cys  Thr  Asp  Leu
               820                      825                      830

AAT  GAG  GAC  TTA  GGT  GTA  TGG  GTG  ATA  TTC  AAG  ATT  AAG  ACA  CAA  GAT                 2544
Asn  Glu  Asp  Leu  Gly  Val  Trp  Val  Ile  Phe  Lys  Ile  Lys  Thr  Gln  Asp
          835                      840                      845

GGC  TAT  GCA  AGA  CTA  GGA  AAT  CTA  GAG  TTT  CTC  GAA  GAG  AAA  CCA  CTA                 2592
Gly  Tyr  Ala  Arg  Leu  Gly  Asn  Leu  Glu  Phe  Leu  Glu  Glu  Lys  Pro  Leu
     850                      855                      860

TTA  GGG  GAA  GCA  CTA  GCT  CGT  GTG  AAA  AGA  GCG  GAG  AAA  AAA  TGG  AGA                 2640
Leu  Gly  Glu  Ala  Leu  Ala  Arg  Val  Lys  Arg  Ala  Glu  Lys  Lys  Trp  Arg
865                      870                      875                      880

GAC  AAA  TGC  GAA  AAA  TTG  GAA  TGG  GAA  ACA  AAT  ATT  GTT  TAT  AAA  GAG                 2688
Asp  Lys  Cys  Glu  Lys  Leu  Glu  Trp  Glu  Thr  Asn  Ile  Val  Tyr  Lys  Glu
                         885                      890                      895

GCA  AAA  GAA  TCT  GTA  GAT  GCT  TTA  TTT  GTA  AAC  TCT  CAA  TAT  GAT  AGA                 2736
Ala  Lys  Glu  Ser  Val  Asp  Ala  Leu  Phe  Val  Asn  Ser  Gln  Tyr  Asp  Arg
               900                      905                      910

TTA  CAA  GCG  GAT  ACG  AAT  ATC  GCG  ATG  ATT  CAT  GCG  GCA  GAT  AAA  CGC                 2784
Leu  Gln  Ala  Asp  Thr  Asn  Ile  Ala  Met  Ile  His  Ala  Ala  Asp  Lys  Arg
          915                      920                      925

GTT  CAT  AGC  ATT  CGA  GAA  GCG  TAT  CTG  CCA  GAG  CTG  TCT  GTG  ATT  CCG                 2832
Val  His  Ser  Ile  Arg  Glu  Ala  Tyr  Leu  Pro  Glu  Leu  Ser  Val  Ile  Pro
     930                      935                      940

GGT  GTC  AAT  GCG  GCT  ATT  TTT  GAA  GAA  TTA  GAA  GGG  CGT  ATT  TTC  ACT                 2880
Gly  Val  Asn  Ala  Ala  Ile  Phe  Glu  Glu  Leu  Glu  Gly  Arg  Ile  Phe  Thr
945                      950                      955                      960

GCA  TTC  TCC  CTA  TAT  GAT  GCG  AGA  AAT  GTC  ATT  AAA  AAT  GGC  GAT  TTC                 2928
Ala  Phe  Ser  Leu  Tyr  Asp  Ala  Arg  Asn  Val  Ile  Lys  Asn  Gly  Asp  Phe
                    965                      970                      975

AAT  AAT  GGC  TTA  TCA  TGC  TGG  AAC  GTG  AAA  GGG  CAT  GTA  GAT  GTA  GAA                 2976
Asn  Asn  Gly  Leu  Ser  Cys  Trp  Asn  Val  Lys  Gly  His  Val  Asp  Val  Glu
               980                      985                      990

GAA  CAG  AAC  AAC  CAT  CGT  TCG  GTC  CTT  GTT  GTT  CCA  GAA  TGG  GAA  GCA                 3024
Glu  Gln  Asn  Asn  His  Arg  Ser  Val  Leu  Val  Val  Pro  Glu  Trp  Glu  Ala
          995                      1000                     1005

GAA  GTG  TCA  CAA  GAA  GTT  CGT  GTT  TGT  CCG  GGT  CGT  GGC  TAT  ATC  CTT                 3072
Glu  Val  Ser  Gln  Glu  Val  Arg  Val  Cys  Pro  Gly  Arg  Gly  Tyr  Ile  Leu
     1010                     1015                     1020

CGT  GTT  ACA  GCG  TAC  AAA  GAG  GGA  TAT  GGA  GAG  GGC  TGT  GTA  ACG  ATT                 3120
Arg  Val  Thr  Ala  Tyr  Lys  Glu  Gly  Tyr  Gly  Glu  Gly  Cys  Val  Thr  Ile
1025                     1030                     1035                     1040

CAT  GAG  ATC  GAA  GAC  AAT  ACA  GAC  GAA  CTG  AAA  TTC  AGC  AAC  TGT  GTA                 3168
His  Glu  Ile  Glu  Asp  Asn  Thr  Asp  Glu  Leu  Lys  Phe  Ser  Asn  Cys  Val
                    1045                     1050                     1055

GAA  GAG  GAA  GTA  TAT  CCA  AAC  AAC  ACG  GTA  ACG  TGT  AAT  AAT  TAT  ACT                 3216
Glu  Glu  Glu  Val  Tyr  Pro  Asn  Asn  Thr  Val  Thr  Cys  Asn  Asn  Tyr  Thr
               1060                     1065                     1070

GCG  ACT  CAA  GAA  GAA  CAT  GAG  GGT  ACG  TAC  ACT  TCC  CGT  AAT  CGA  GGA                 3264
Ala  Thr  Gln  Glu  Glu  His  Glu  Gly  Thr  Tyr  Thr  Ser  Arg  Asn  Arg  Gly
          1075                     1080                     1085
```

-continued

| | | | | | | | | | | | | | | | | |
|---|---|---|---|---|---|---|---|---|---|---|---|---|---|---|---|---|
| TAT | GAC | GAA | GCC | TAT | GAA | AGC | AAT | TCT | TCT | GTA | CAT | GCG | TCA | GTC | TAT | 3312 |
| Tyr | Asp | Glu | Ala | Tyr | Glu | Ser | Asn | Ser | Ser | Val | His | Ala | Ser | Val | Tyr | |
| | 1090 | | | | 1095 | | | | | | 1100 | | | | | |
| GAA | GAA | AAA | TCG | TAT | ACA | GAT | AGA | CGA | AGA | GAG | AAT | CCT | TGT | GAA | TCT | 3360 |
| Glu | Glu | Lys | Ser | Tyr | Thr | Asp | Arg | Arg | Arg | Glu | Asn | Pro | Cys | Glu | Ser | |
| 1105 | | | | | 1110 | | | | | 1115 | | | | | 1120 | |
| AAC | AGA | GGA | TAT | GGG | GAT | TAC | ACA | CCA | CTA | CCA | GCT | GGC | TAT | GTG | ACA | 3408 |
| Asn | Arg | Gly | Tyr | Gly | Asp | Tyr | Thr | Pro | Leu | Pro | Ala | Gly | Tyr | Val | Thr | |
| | | | | 1125 | | | | | 1130 | | | | | 1135 | | |
| AAA | GAA | TTA | GAG | TAC | TTC | CCA | GAA | ACC | GAT | AAG | GTA | TGG | ATT | GAG | ATC | 3456 |
| Lys | Glu | Leu | Glu | Tyr | Phe | Pro | Glu | Thr | Asp | Lys | Val | Trp | Ile | Glu | Ile | |
| | | | 1140 | | | | | 1145 | | | | | 1150 | | | |
| GGA | GAA | ACG | GAA | GGA | ACA | TTC | ATC | GTG | GAC | AGC | GTG | GAA | TTA | CTT | CTT | 3504 |
| Gly | Glu | Thr | Glu | Gly | Thr | Phe | Ile | Val | Asp | Ser | Val | Glu | Leu | Leu | Leu | |
| | | 1155 | | | | | | 1160 | | | | 1165 | | | | |
| ATG | GAG | GAA | | | | | | | | | | | | | | 3513 |
| Met | Glu | Glu | | | | | | | | | | | | | | |
| | 1170 | | | | | | | | | | | | | | | |

( 2 ) INFORMATION FOR SEQ ID NO:4:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

GCTGAAGAAC TTCCTATTCG TGGTGGTGAG C        31